US012569114B2

(12) United States Patent
Srivastava et al.

(10) Patent No.: US 12,569,114 B2
(45) Date of Patent: Mar. 10, 2026

(54) METHODS AND SYSTEMS FOR INTRAOPERATIVELY SELECTING AND DISPLAYING CROSS-SECTIONAL IMAGES

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Vaibhav Srivastava, Andover, MA (US); Brian William Quist, Salem, NH (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 0 days.

(21) Appl. No.: 18/782,784

(22) Filed: Jul. 24, 2024

(65) Prior Publication Data

US 2025/0031942 A1     Jan. 30, 2025

Related U.S. Application Data

(60) Provisional application No. 63/515,623, filed on Jul. 26, 2023.

(51) Int. Cl.
| | |
|---|---|
| *A61B 34/10* | (2016.01) |
| *A61B 1/00* | (2006.01) |
| *A61B 34/00* | (2016.01) |

(52) U.S. Cl.
CPC .... *A61B 1/000094* (2022.02); *A61B 1/00045* (2013.01); *A61B 34/10* (2016.02); *A61B 34/25* (2016.02); *A61B 2034/105* (2016.02); *A61B 2034/252* (2016.02)

(58) Field of Classification Search
CPC .......... A61B 1/000094; A61B 1/00045; A61B 34/10; A61B 34/25; A61B 2034/105; A61B 2034/252
See application file for complete search history.

(56) References Cited

U.S. PATENT DOCUMENTS

| | | | |
|---|---|---|---|
| 9,498,132 | B2 | 11/2016 | Maier-Hein et al. |
| 10,398,514 | B2 | 9/2019 | Ryan et al. |
| 10,987,175 | B2 | 4/2021 | Britton et al. |
| 11,071,596 | B2 | 7/2021 | Ryan et al. |
| 11,432,878 | B2 | 9/2022 | Hladio et al. |
| 12,211,151 | B1 * | 1/2025 | Chiou ................... G06T 19/003 |

(Continued)

FOREIGN PATENT DOCUMENTS

| | | |
|---|---|---|
| WO | 2022076790 A1 | 4/2022 |
| WO | 2024098058 A1 | 5/2024 |

OTHER PUBLICATIONS

Raposo, Carolina, et al., "Video-based Computer Navigation in Knee Arthroscopy for Patient-specific ACL Reconstruction", International Journal of Computer Assisted Radiology and Surgery, Jun. 2019, 17 pages.

(Continued)

*Primary Examiner* — Thai Q Tran
*Assistant Examiner* — Jose M Mesa
(74) *Attorney, Agent, or Firm* — Dickinson Wright PLLC

(57) ABSTRACT

Some examples are directed to methods and related systems for intraoperatively selecting and displaying cross-sectional images.

24 Claims, 13 Drawing Sheets

(56) References Cited

U.S. PATENT DOCUMENTS

| | | |
|---|---|---|
| 2018/0049622 A1 | 2/2018 | Ryan et al. |
| 2021/0169578 A1 | 6/2021 | Calloway et al. |
| 2021/0169605 A1 | 6/2021 | Calloway et al. |
| 2021/0346117 A1 | 11/2021 | Poltaretskyi et al. |
| 2022/0375114 A1* | 11/2022 | Hunter ............. A61B 1/000094 |
| 2023/0301719 A1* | 9/2023 | Murphy ................. G06F 3/012 |
| 2024/0189042 A1 | 6/2024 | Fouts et al. |

OTHER PUBLICATIONS

Turan, Mehmet, et al., "Magnetic and Optical Tracking: Magnetic-Visual Sensor Fusion based Medical SLAM for Endoscopic Capsule Robot", Computer Vision and Pattern Recognition, May 2017, 23 pages.

OpenIGTlink, "OpenIGTLink: Open Network Interface for Image-Guided Therapy", http://openigtlink.org/, accessed May 9, 2024.

Lin, Bingxiong, et al., "Video-based 3D Reconstruction, Laparoscope Localization and Deformation Recovery for Abdominal Minimally Invasive Surgery: A Survey", International Journal of Medical Robotics and Computer Assisted Surgery, Mar. 2015, 21 pages.

Marmol, Andres, et al., "ArthroSLAM: Multi-sensor Robust Visual Localization for Minimally Invasive Orthopedic Surgery", International Conference on Intelligent Robots and Systems, Oct. 2018, 9 pages.

\* cited by examiner

414

$(X, Y)$

SLICE S $(O_x, O_y, O_z)$ $\Delta z$ $\Delta x$ $\Delta y$

S

S

S

METHODS AND SYSTEMS FOR INTRAOPERATIVELY SELECTING AND DISPLAYING CROSS-SECTIONAL IMAGES

CROSS-REFERENCE TO RELATED APPLICATION

This application claims the benefit of priority to U.S. Provisional Patent Application No. 63/515,623, titled "Methods and Systems For Intraoperatively Selecting and Displaying Cross-Sectional Images," filed Jul. 26, 2023, which is incorporated herein by reference in its entirety.

BACKGROUND

The anterior cruciate ligament (ACL) serves as the primary mechanical restraint in the knee to resist anterior translation of the tibia relative to the femur. Similarly, the posterior cruciate ligament (PCL) serves as a mechanical restraint to resist posterior translation of the tibia relative to the femur. These cruciate ligaments contribute significantly to knee stability, and ACL injury is quite common. Most ACL injuries are complete tears of the ligament.

As ACL injuries occur often in patients that are young and active, reconstruction of the ACL is performed to enable a return to activity. The goal is to restore stability of the knee and reduce the chances of further damage to the meniscus and articular cartilage that may lead to degenerative osteoarthritis. Reconstruction may consist of placement of a substitute graft (e.g., autograft from either the central third of the patellar tendon or the hamstring tendons). The ends of the graft are placed into respective tunnels prepared through the femur and the tibia. The ends of the graft may be attached using interference screws or a suspensory fixation device like the ENDOBUTTON™ brand fixation devices manufactured by Smith & Nephew of Andover, Massachusetts, USA.

One challenge in ACL reconstruction is where the tunnels should be placed. The native ACL consists of 2 major bundles—the anteromedial (AM) and the posterolateral (PL) bundle. Often, the goal of the surgery is to place the reconstruction in an anatomical location, for example, placing a single tunnel within the footprint of the native ACL attachment site. In other cases, reconstruction may involve creating two tunnels in both the femur and tibia in an attempt to recreate the two native bundles.

It is generally the case that an ACL repair starts with imaging (e.g., X-ray imaging, computed tomography (CT) imaging, magnetic resonance imaging (MRI)) of the knee of the patient, including the relevant anatomy like the lower portion of the femur, the upper portion of the tibia, and the articular cartilage. An outcome of such imaging is a plurality of cross-sectional images of the relevant anatomy. A surgeon may wish to plan for ACL repair by studying the contents of the cross-sectional images, which may be stored and organized as stacks of "slices" along respective ones of the axial, sagittal, and coronal axes with respect to the anatomy. These cross-sectional images may additionally be processed to produce a volumetric or three-dimensional model of the anatomy. MRI imaging, for example, can be segmented from the image slices such that a volumetric model or three-dimensional model of the anatomy is created. A number of segmentation technologies may be used to create the three-dimensional model. More specifically to the example of ACL repair and specifically selecting a tunnel path through the femur, a three-dimensional bone model of the lower portion of the femur, including the femoral condyles, may be created. Using the three-dimensional bone model, an operative plan may be created that comprises choosing one or more planned-tunnel paths through respective bones, including locations of the apertures of the bone(s) that define the ends of the tunnel. The three-dimensional bone model and the planned-tunnel paths created preoperatively may be viewed by the surgeon intraoperatively.

During surgery, in addition to viewing the three-dimensional model of the anatomy, the planned tunnel paths, and the actual anatomy as viewed using, for example, an endoscope, a surgeon may wish to view the cross-sectional images. However, the surgeon may struggle to correlate the anatomy as captured in the cross-sectional images with the actual anatomy.

SUMMARY

One example is intraoperative method comprising receiving, by a surgical controller, a three-dimensional bone model of a bone; receiving, by the surgical controller, a set of cross-sectional images of the bone; and during a surgical procedure: receiving, by the surgical controller, video frames of a bone and of an instrument as viewed by an endoscope and attached camera head, the video frames including video frames of an origin marker and the instrument, wherein the three-dimensional bone model is registered to the bone; and selecting and displaying, on at least one display device, at least one of the cross-sectional images of the bone depending on position and orientation of the instrument with respect to the origin marker in the video frames.

In the example method, the origin marker may be a bone fiducial coupled to the bone.

In the example method, the origin marker may be a unique anatomical structure.

In the example method, the unique anatomical structure is a unique bone structure.

In the example method, the video frames may include video frames of an instrument fiducial coupled to the instrument, and further wherein the selecting and displaying is depending on position and orientation of the instrument fiducial with respect to the origin marker in the video frames.

In the example method, the set of cross-sectional images of the bone include an axial series of cross-sectional images, a sagittal series of cross-sectional images, and a coronal series of cross-sectional images.

In the example method, the selecting and displaying may comprise selecting from and displaying the cross-sectional images of the bone from each of the axial series, the sagittal series, and the coronal series.

The example method may further comprise overlaying, on selected and displayed cross-sectional images, an indicia corresponding to a location of a tip of the instrument at a time of display.

The example method may further comprise displaying, on the at least one display device, a visual representation of the three-dimensional bone model and a visual representation of a position and an orientation of the instrument with respect to the three-dimensional bone model depending on a position and an orientation of the instrument with respect to the origin marker in the video frames.

In the example method, the selecting and displaying may comprise determining locations of a tip of the instrument in respective video frames; transforming each of the locations of the tip of the instrument in respective video frames to counterpart locations with respect to the three-dimensional bone model; transforming each of the counterpart locations with respect to the three-dimensional bone model to a respective at least one cross-sectional image in the set of cross-sectional images of the bone; and displaying the respective at least one cross-sectional image.

In the example method, the set of cross-sectional images of the bone includes an axial series of cross-sectional images, a sagittal series of cross-sectional images, and a coronal series of cross-sectional images; and transforming each of the counterpart locations with respect to the three-dimensional bone model to a respective at least one cross-sectional image in the set of cross-sectional images of the bone may comprise, for each of a plurality of the video frames: transforming each of the counterpart locations with respect to the bone model to each of a corresponding cross-sectional image in the axial series, a corresponding cross-sectional image in the sagittal series, and a corresponding cross-sectional image in the coronal series; and displaying the respective at least one cross-sectional image may comprise, for each of the plurality of the video frames: displaying each of the corresponding cross-sectional image in the axial series, the corresponding cross-sectional image in the sagittal series, and the corresponding cross-sectional image in the coronal series.

In the example method, the set of cross-sectional images may comprise preoperative-captured cross-sectional images.

Yet another example is a surgical controller comprising: processing structure configured to couple to at least one display device; a memory coupled to the processing structure, the memory storing instructions that, when executed by the processing structure, cause the processing structure to: receive a three-dimensional bone model of a bone; receive a set of cross-sectional images of the bone; and during a surgical procedure: receive video frames of a bone and of an instrument as viewed by an endoscope and attached camera head, the video frames including video frames of an origin marker and the instrument, wherein the three-dimensional bone model is registered to the bone; and select and display, on the at least one display device, at least one of the cross-sectional images of the bone depending on position and orientation of the instrument with respect to the origin marker in the video frames.

In the example surgical controller, the origin marker may be a bone fiducial coupled to the bone.

In the example surgical controller, the origin marker may be a unique anatomical structure.

In the example surgical controller, the unique anatomical structure may be a unique bone structure.

In the example surgical controller, the video frames include video frames of an instruction fiducial coupled to the instrument, and further wherein the selecting and displaying is depending on position and orientation of the instrument fiducial with respect to the origin marker in the video frames.

In the example surgical controller, the set of cross-sectional images of the bone may include an axial series of cross-sectional images, a sagittal series of cross-sectional images, and a coronal series of cross-sectional images.

In the example surgical controller, the instructions that, when executed by the processing structure, cause the processing structure to select and display may comprise: instructions that, when executed by the processing structure, cause the processing structure to select from and display the cross-sectional images of the bone from each of the axial series, the sagittal series, and the coronal series.

In the example surgical controller, the memory may store instructions that, when executed by the processing structure, cause the processing structure to: overlay, on selected and displayed cross-sectional images, an indicia corresponding to a location of a tip of the instrument at the time of display.

In the example surgical controller, the memory may store instructions that, when executed by the processing structure, cause the processing structure to: display, on the at least one display device, a visual representation of the three-dimensional bone model and a visual representation of a position and an orientation of the instrument with respect to the three-dimensional bone model depending on a position and an orientation of the instrument with respect to the origin marker in the video frames.

In the example surgical controller, the instructions that, when executed by the processing structure, cause the processing structure to select and display may comprise instructions that, when executed by the processing structure, cause the processing structure to: determine locations of a tip of the instrument in respective video frames; transform each of the locations of the tip of the instrument in respective video frames to counterpart locations with respect to the three-dimensional bone model; transform each of the counterpart locations with respect to the three-dimensional bone model to a respective at least one cross-sectional image in the set of cross-sectional images of the bone; and display the respective at least one cross-sectional image.

In the example surgical controller, the set of cross-sectional images of the bone may include an axial series of cross-sectional images, a sagittal series of cross-sectional images, and a coronal series of cross-sectional images; and the instructions that, when executed by the processing structure, cause the processing structure to transform may comprise instructions that, when executed by the processing structure, cause the processing structure to: for each of a plurality of the video frames: transform each of the counterpart locations with respect to the three-dimensional bone model to each of a corresponding cross-sectional image in the axial series, a corresponding cross-sectional image in the sagittal series, and a corresponding cross-sectional image in the coronal series; and the instructions that, when executed by the processing structure, cause the processing structure to display may comprise instructions that, when executed by the processing structure, cause the processing structure to: display each of the corresponding cross-sectional image in the axial series, the corresponding cross-sectional image in the sagittal series, and the corresponding cross-sectional image in the coronal series.

In the example surgical controller, the set of cross-sectional images may comprise preoperative-captured cross-sectional images.

BRIEF DESCRIPTION OF THE DRAWINGS

For a detailed description of example embodiments, reference will now be made to the accompanying drawings in which.

DEFINITIONS

Figure 2:
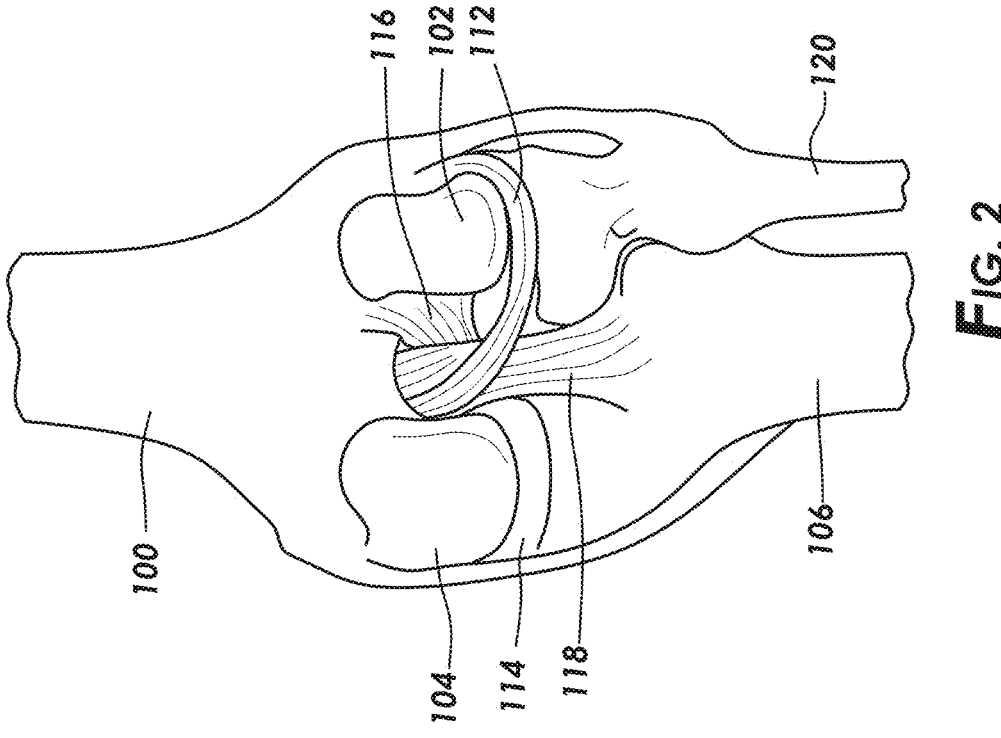
FIG. 2 shows a posterior or back elevation view of the right knee.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

"Receiving . . . a . . . location" shall mean receiving data indicative of location on a bone within a coordinate space (e.g., a coordinate space of a view of an endoscope). Thus, example systems and methods may "receive . . . a revised-tunnel entry location" being data indicative of a proposed location of a tunnel entry point within a three-dimensional coordinate space. Other example systems and methods may "receive . . . a plurality of locations on a bone" being data indicative locations of an outer surface of a bone as part of registering a bone to a three-dimensional bone model.

An endoscope having "a single optical path" through an endoscope shall mean that the endoscope is not a stereoscopic endoscope having two distinct optical paths separated by an interocular distance at the light collecting end of the endoscope. The fact that an endoscope has two or more optical members (e.g., glass rods, optical fibers) forming a single optical path shall not obviate the status as a single optical path.

"Throughbore" shall mean an aperture or passageway through an underlying device. However, the term "throughbore" shall not be read to imply any method of creation. Thus, a throughbore may be created in any suitable way, such as drilling, boring, laser drilling, or casting.

"Counterbore" shall mean an aperture or passageway into an underlying device. In cases in which the counterbore intersects another aperture (e.g., a throughbore), the counterbore may thus define an internal shoulder. However, the term "counterbore" shall not be read to imply any method of creation. A counterbore may be created in any suitable way, such as drilling, boring, laser drilling, or casting.

"Processing structure" shall mean a single processing device, processor, microprocessing device, microprocessor, computing device, computer, computer system or other device that, like these, can be instructed to and/or configured to conduct computational processing, or an arrangement of multiple processing devices, processors, microprocessing devices, microprocessors, computing devices, computers, computer systems and/or other devices that, like these, can be instructed to and/or configured to conduct computational processing.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various examples are directed to methods and systems for intraoperatively selecting and displaying cross-sectional images. In examples, the cross-sectional images are captured preoperatively.

The various examples were developed in the context of ACL repair, and thus the discussion below is based on the developmental context. However, the techniques are applicable to many types of ligament repair, such as medial collateral ligament repair, lateral collateral ligament repair, and posterior cruciate ligament repair. Moreover, the various example methods and systems can also be used for planning and placing anchors to reattach soft tissue, such as reattaching the labrum of the hip, the shoulder, or the meniscal root. Furthermore, the various example methods and systems can also be used for planning and navigation of instruments with respect to an anatomy. Thus, the description and developmental context shall not be read as a limitation of the applicability of the teachings. In order to orient the reader, the specification first turns a description of the knee.

Figure 1:
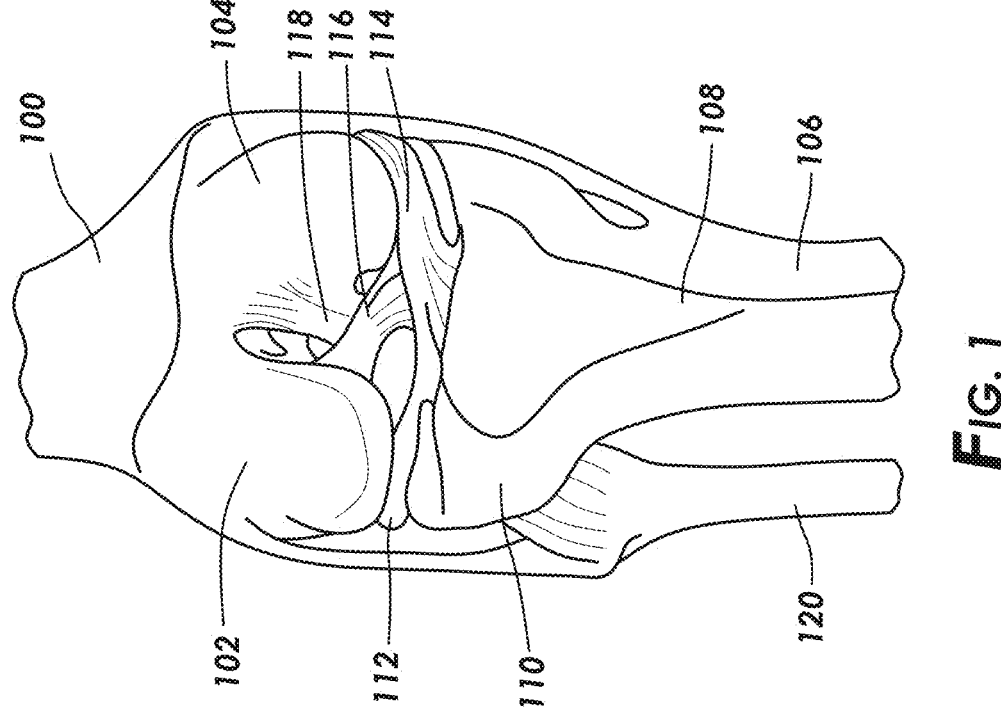
FIG. 1 shows an anterior or front elevation view of right knee, with the patella removed.

FIG. 1 shows an anterior or front elevation view of a right knee, with the patella removed. In particular, visible in FIG. 1 is lower portion of the femur 100 including the outer or lateral condyle 102 and the inner or medial condyle 104. The femur 100 and condyles 102 and 104 are in operational relationship to a tibia 106 including the tibial tuberosity 108 and Gerdy's tubercle 110. Disposed between the femoral condyles 102 and 104 and the tibia 106 are the lateral meniscus 112 and the medial meniscus 114. Several ligaments are also visible in the view of FIG. 1, such as the ACL 116 extending from the lateral side of femoral notch to the medial side of the tibia 106. Oppositely, the posterior cruciate ligament 118 extends from medial side of the femoral notch to the tibia 106. Also visible is the fibula 120, and several additional ligaments that are not specifically numbered.

FIG. 2 shows a posterior or back elevation view of the right knee. In particular, visible in FIG. 2 is lower portion of the femur 100 including the lateral condyle 102 and the medial condyle 104. The femur 100 and femoral condyles 102 and 104 again are in operational relationship to the tibia 106, and disposed between the femoral condyles 102 and 104 and the tibia 106 are the lateral meniscus 112 and the medial meniscus 114. FIG. 2 further shows the ACL 116 extending from the lateral side of femoral notch to the medial side of the tibia 106, though the attachment point to the tibia 106 is not visible. The posterior cruciate ligament 118 extends from medial side of the femoral notch to the tibia 106, though the attachment point to the femur 100 not visible. Again, several additional ligaments are shown that are not specifically numbered.

The most frequent ACL injury is a complete tear of the ligament. Treatment involves reconstruction of the ACL by placement of a substitute graft (e.g., autograft from either the patellar tendon, quad tendon, or the hamstring tendons). The graft is placed into tunnels prepared within the femur 100 and the tibia 106. The current standard of care for ACL repair is to locate the tunnels such that the tunnel entry point for the graft is at the anatomical attachment location of the native ACL. Such tunnel placement at the attachment location of the native ACL attempts to recreate original knee kinematics. In arthroscopic surgery, the location of the tunnel through the tibia 106 is relatively easy to reach, particularly when the knee is bent or in flexion. However, the tunnel through the femur 100 resides within the intercondylar notch. Depending upon the physical size of the patient and the surgeon's selection for location of the port through the skin, and through which the various instruments are inserted into the knee, it may be difficult to reach the attachment location of the native ACL to the femur 100.

Figure 3:
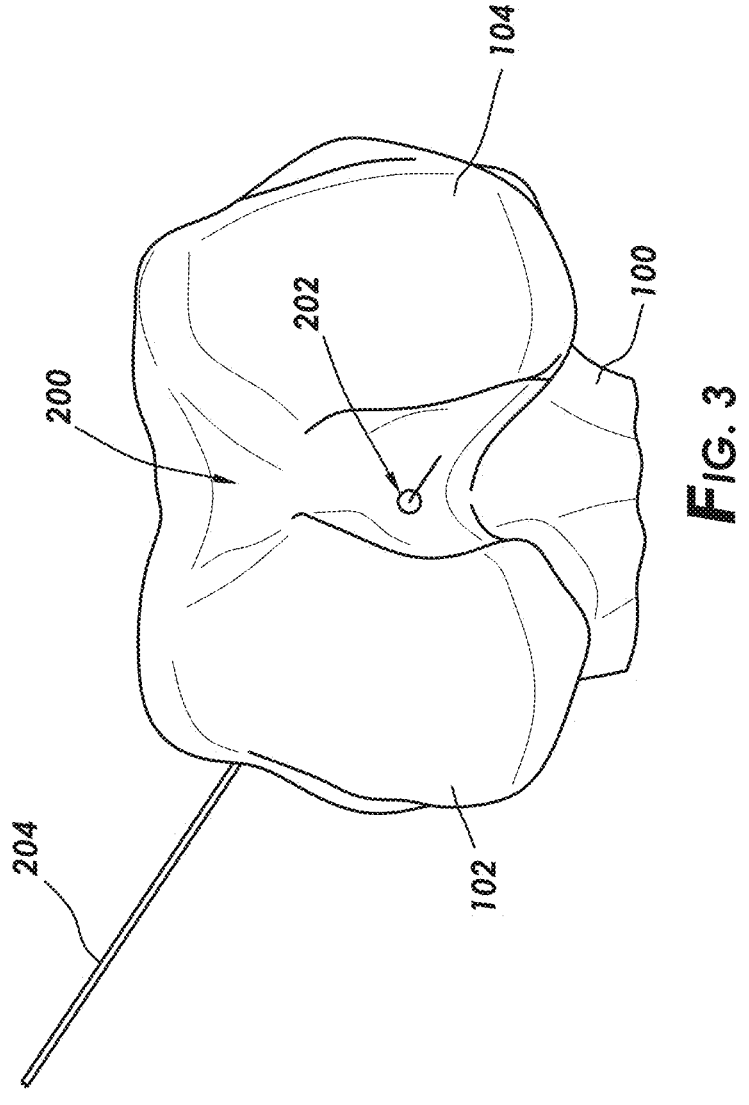
FIG. 3 shows a view of the femur from below and looking into the intercondylar notch.

FIG. 3 shows a view of the femur from below and looking into the intercondylar notch. In particular, visible in FIG. 3 are the lateral condyle 102 and the medial condyle 104. Defined between the femoral condyles 102 and 104 is the femoral notch 200. The femoral tunnel may define an inside aperture 202 within the femoral notch 200, the inside aperture 202 closer to the lateral condyle 102 and displaced into the posterior portion of the femoral notch 200. The femoral tunnel extends through the femur 100 and forms an outside aperture on the outside or lateral surface of the femur 100 (the outside aperture not visible in FIG. 3). FIG. 3 shows an example drill wire 204 that may be used to create an initial tunnel or pilot hole. Once the surgeon verifies that the pilot hole is closely aligned with a planned-tunnel path, the femoral tunnel is created by boring or reaming with another instrument (e.g., a reamer) that may use the drill wire 204 as a guide. In some cases, a socket or counter-bore is created on the intercondylar notch side to accommodate the width of the graft that extends into the bone, and that counterbore may also be created using another instrument (e.g., reamer) that may use the drill wire 204 as a guide.

Drilling of a tunnel may take place from either direction. Considering the femoral tunnel again as an example, the tunnel may be drilled from the outside or lateral portion of the femur 100 toward and into the femoral notch 200, which is referred to as an "outside-in" procedure. Oppositely, the example femoral tunnel may be drilled from the inside of the femoral notch 200 toward and to the lateral portion of the femur 100, which is referred as an "inside-out" procedure. The various examples discussed below are equally applicable to outside-in or inside-out procedures. Outside-in procedures may additionally use a device which holds the drill wire on the outside portion, and physically shows the expected tunnel location of the inside aperture within the knee. However, the device for the outside-in procedure is difficult to use in arthroscopic procedures, and thus many arthroscopic repairs use the inside-out procedure. The further examples discussed below are thus based on an inside-out procedure, but such should not be read as a limitation. The specification now turns to an example surgical system.

Figure 4:
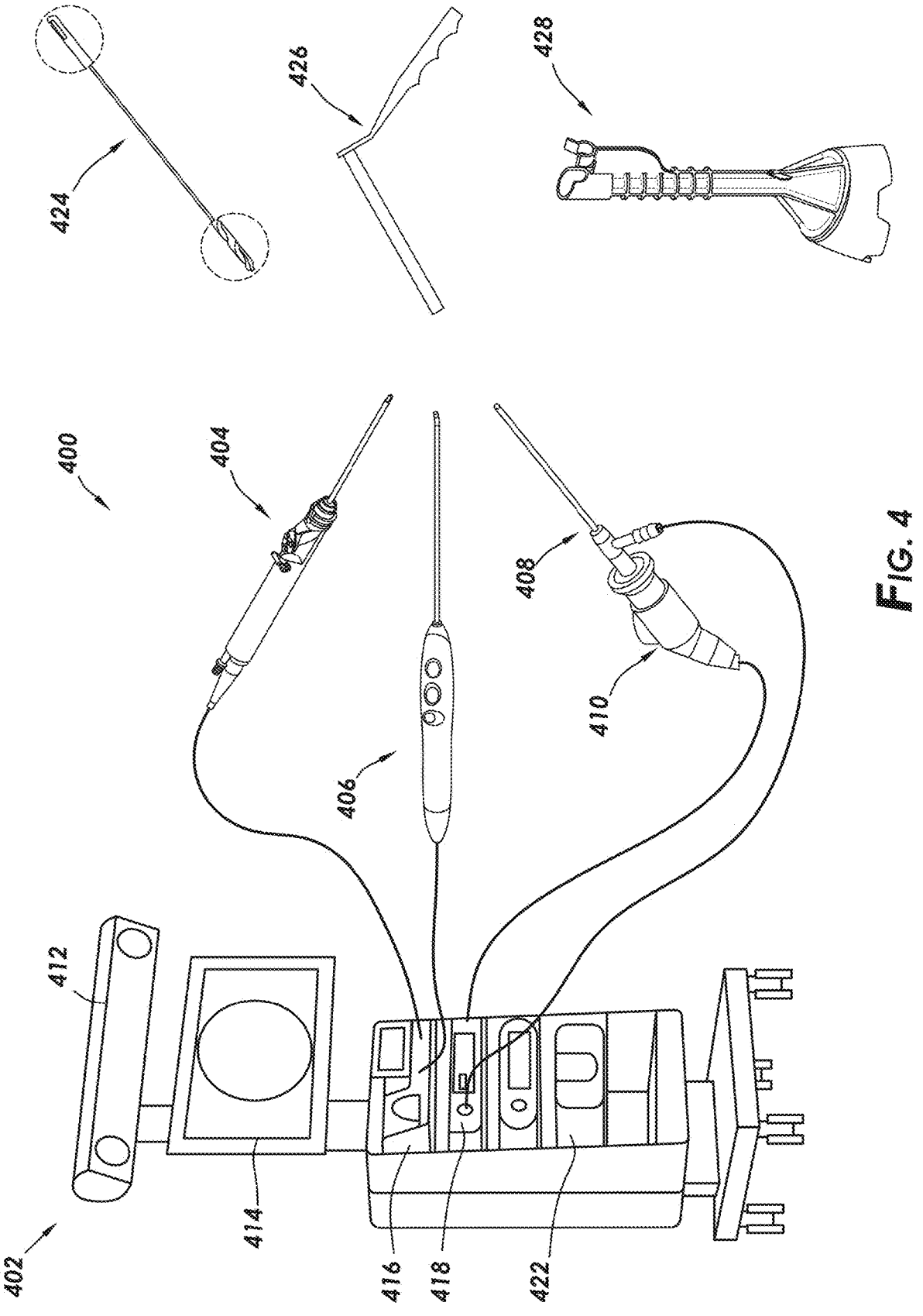
FIG. 4 shows a surgical system in accordance with at least some embodiments.

FIG. 4 shows a surgical system (not to scale) in accordance with at least some embodiments. In particular, the example surgical system 400 comprises a tower or device cart 402, an example mechanical resection instrument 404, an example plasma-based ablation instrument (hereafter just ablation instrument 406), and an endoscope in the example form of an arthroscope 408 and attached camera head 410. The endoscope 408 defines a light connection or light post 420 to which light is provided, and the light is routed internally within the endoscope 408 to illuminate a surgical field at the distal end of the endoscope 408. The device cart 402 may comprise a camera 412 (illustratively shown as a stereoscopic camera), a display device 414, a resection controller 416, and a camera control unit (CCU) together with an endoscopic light source and video controller 418. In example cases the CCU and video controller 418 provides light to the light post 420 of the arthroscope 408, displays images received from the camera head 410. In example cases, the CCU and video controller 418 also implements various additional aspects, such as calibration of the arthroscope and camera head, displaying planned-tunnel paths on the display device 414, receiving revised-tunnel entry locations, calculating revised-tunnel paths, and calculating and displaying various parameters that show the relationship between the revised-tunnel path and the planned-tunnel path. Thus, the CCU and video controller is hereafter referred to as surgical controller 418. In other cases, however, the CCU and video controller may be a separate and distinct system from the controller that handles aspects of intraoperative changes, yet the separate devices would nevertheless be operationally coupled.

The example device cart 402 further includes a pump controller 422 (e.g., single or dual peristaltic pump). Fluidic connections of the mechanical resection instrument 404 and ablation instrument 406 are not shown so as not to unduly complicate the figure. Similarly, fluidic connections between the pump controller 422 and the patient are not shown so as not to unduly complicate the figure. In the example system, both the mechanical resection instrument 404 and the ablation instrument 406 are coupled to the resection controller 416 being a dual-function controller. In other cases, however, there may be a mechanical resection controller separate and distinct from an ablation controller. The example devices and controllers associated with the device cart 402 are merely examples, and other examples include vacuum pumps, patient-positioning systems, robotic arms holding various instruments, ultrasonic cutting devices and related controllers, patient-positioning controllers, and robotic surgical systems.

FIG. 4 further shows additional instruments that may be present during an example ACL repair. In particular, FIG. 4 shows an example guide wire or drill wire 424 and an aimer 426. The drill wire 424 may be used to create an initial or pilot tunnel through the bone. In some cases, the diameter of the drill wire may be about 2.4 millimeters (mm), but larger and smaller diameters for the drill wire 424 may be used. The example drill wire 424 is shown with magnified portions on each end, one to show the cutting elements on the distal end of the drill wire 242, and another magnified portion to show a connector for coupling to chuck of a drill. Once the surgeon drills the pilot tunnel, the surgeon and/or the surgical controller 418 (discussed more below) may then assess whether the pilot tunnel matches or closes matches the planned-tunnel path. If the pilot tunnel is deemed sufficient, then the drill wire 424 may be used as a guide for creating the full-diameter throughbore for the tunnel, and possibly also for creating a counterbore associated with intercondylar notch to accommodate the graft. While in some cases the drill wire alone may be used when creating the pilot tunnel, in yet still other cases the surgeon may use the aimer 426 to help guide and place the drill wire 424 at the designed tunnel-entry location.

FIG. 4 also shows that the example system may comprise a calibration assembly 428. As explained in further detail in PCT Publication No. WO/2023/034194 to Quist et al. ("Quist"), the contents of which are incorporated herein by reference, the calibration assembly 428 may be used to detect optical distortion in images received by the surgical controller 418 through the arthroscope 408 and attached camera head 410. Additional tools and instruments will be present, such as a drill for drilling with the drill wire 424, various reamers for creating the throughbore and counterbore aspects of the tunnel, and various tools for suturing and anchoring the graft in place. These additional tools and instruments are not shown so as not to further complicate the figure.

The specification now turns to a workflow for an example ACL repair. The workflow may be conceptually divided into a preoperative planning and intraoperative repair. The intraoperative repair workflow may be further conceptually divided into optical system calibration, model registration, intraoperative tunnel-path planning, intraoperative tunnel creation, and intraoperative tunnel placement analysis. Each will be addressed in turn.

Planning

In accordance with various examples, an ACL repair starts with imaging (e.g., X-ray imaging, computed tomography (CT), magnetic resonance imaging (MRI)) of the knee of the patient, including the relevant anatomy like the lower portion of the femur, the upper portion of the tibia, and the articular cartilage. The discussion that follows assumes MRI imaging, but again many different types of imaging may be used. The MRI imaging can be segmented from the image slices such that a volumetric model or three-dimensional model of the anatomy is created. Any suitable currently available, or after developed, segmentation technology may be used to create the three-dimensional model. More specifically to the example of ACL repair and specifically selecting a tunnel path through the femur, a three-dimensional bone model of the lower portion of the femur, including the femoral condyles, is created.

Using the three-dimensional bone model, an operative plan is created that comprises choosing a planned-tunnel path through the femur, including locations of the apertures of the bone that define the ends of the tunnel. For an example inside-out repair, the aperture within the femoral notch is the entry location for the drilling, and the aperture on the lateral surface of the femur is the exit location. For an outside-in repair, the entry and exit locations for drilling are swapped. Still assuming an inside-out repair, the entry location may be selected to be the same as, or close to, the attachment location of the native ACL to the femur within the femoral notch. In some cases, selecting the entry location within the femoral notch may involve use of a Bernard & Hertel Quadrant or grid placed on a fluoroscopic image, or placing the Bernard & Hertel Quadrant on a simulated fluoroscopic image created from the three-dimensional bone model. Based on use of the Bernard & Hertel Quadrant, an entry location for the tunnel is selected. For an inside-out repair, selection of the exit location is less restrictive, not only because the portion of the tunnel proximate to the exit location is used for placement of the anchor for the graft, but also because the exit location is in approximately centered in the femur (considered anteriorly to posteriorly), and thus issues of bone wall thickness at the exit location are of less concern. In some cases, a three-dimensional bone model of the proximal end of the tibia is also created, and the surgeon may likewise choose planned-tunnel path(s) through the tibia.

The results of the planning may comprise: a three-dimensional bone model of the distal end of the femur; a three-dimensional bone model for a proximal end of the tibia; an entry location and exit location through the femur and thus a planned-tunnel path for the femur; and an entry location and exit location through the tibia and thus a planned-tunnel path through the tibia. Other surgical parameters may also be selected during the planning, such as tunnel throughbore diameters, tunnel counterbore diameters and depth, desired post-repair flexion, and the like, but those additional surgical parameters are omitted so as not to unduly complication the specification.

Intraoperative Repair

The specification now turns to intraoperative aspects. The intraoperative aspects include steps and procedures for setting up the surgical system to perform the various repairs. It is noted, however, that some of the intraoperative aspects (e.g., optical system calibration), may take place before any ports or incisions are made through the patient's skin, and in fact before the patient is wheeled into the surgical room. Nevertheless, such steps and procedures may be considered intraoperative as they take place in the surgical setting and with the surgical equipment and instruments used to perform the actual repair.

The example ACL repair is conducted arthroscopically and is computer-assisted in the sense the surgical controller 418 is used for arthroscopic navigation within the surgical site. More particularly, in example systems the surgical controller 418 provides computer-assistance during the ligament repair by tracking location of various objects within the surgical site, such as the location of the bone within the three-dimensional coordinate space of the view of the arthroscope, and location of the various instruments (e.g., the drill wire 424, the aimer 426) within the three-dimensional coordinate space of the view of the arthroscope. The specification turns to brief description of such tracking techniques.

Figure 5:
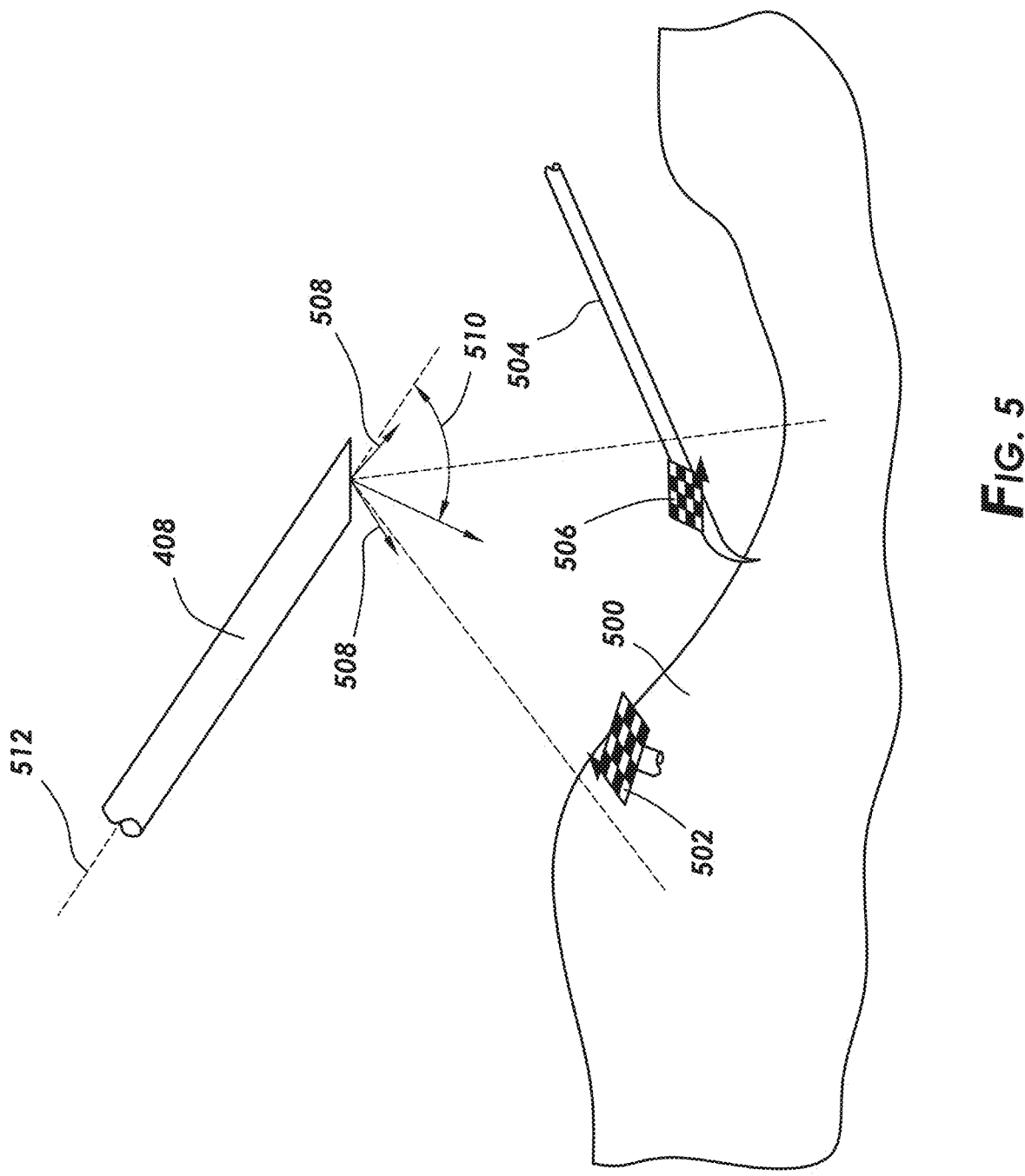
FIG. 5 shows a conceptual drawing of a surgical site with various objects within the surgical site tracked, in accordance with at least some embodiments.

FIG. 5 shows a conceptual drawing of a surgical site with various objects within the surgical site. In particular, visible in FIG. 5 is a distal end of the arthroscope 408, a portion of a bone 500 (e.g., femur), a bone fiducial 502 within the surgical site, a touch probe 504, and a probe fiducial 506. Each is addressed in turn.

The distal end of the arthroscope 408 is designed and constructed to illuminate the surgical site with visible light received by way of the light post 420 (FIG. 4). In the example of FIG. 5, the illumination is illustrated by arrows 508. The illumination provided to the surgical site is reflected by various objects and tissues within the surgical site, and the reflected light that returns to the distal end enters the arthroscope 408, propagates along an optical channel within the arthroscope 408, and is eventually incident upon a capture array within the camera head 410 (FIG. 4). The images detected by the capture array within the camera head 410 are sent electronically to the surgical controller 418 (FIG. 4) and displayed on the display device 414 (FIG. 4). In accordance with example systems, the arthroscope 408 has a single optical path through the arthroscope for capturing images of the surgical site, notwithstanding that the single optical path may be constructed of two or more optical members (e.g., glass rods, optical fibers). That is to say, in example systems and methods the computer-assisted navigation provided by the arthroscope 408, camera head 410, and surgical controller 418 is provided with the arthroscope 408 that is not a stereoscopic endoscope having two distinct optical paths separated by an interocular distance at the distal end endoscope.

During a surgical procedure, a surgeon selects an arthroscope with a viewing direction beneficial for the planned surgical procedure. Viewing direction refers to a line residing at the center of an angle subtended by the outside edges or peripheral edges of the view of an endoscope. The viewing direction for some arthroscopes is aligned with the longitudinal central axis of the arthroscope, and such arthroscopes are referred to as "zero degree" arthroscopes (e.g., the angle between the viewing direction and the longitudinal central axis of the arthroscope is zero degrees). The viewing direction of other arthroscopes forms a non-zero angle with the longitudinal central axis of the arthroscope. For example, for a 30° arthroscope the viewing direction forms a 30° angle to the longitudinal central axis of the arthroscope, the angle measured as an obtuse angle beyond the distal end of the arthroscope. In many cases for ACL repair, the surgeon selects a 30° arthroscope or a 45° arthroscope based on location the port created through the skin of the patient. In the example of FIG. 5, the view angle 510 of the arthroscope 408 forms a non-zero angle to the longitudinal central axis 512 of the arthroscope 408.

Still referring to FIG. 5, within the view of the arthroscope 408 is a portion of the bone 500, along with the bone fiducial 502, the touch probe 504, and the probe fiducial 506. In this example, the bone fiducial 502 serves as an origin marker that specifies the origin and orientation of the three-dimensional coordinate space of the view of the arthroscope 408 and with which a three-dimensional bone model may be registered. Other forms of origin markers may be used, as will be described. However, the following description proceeds with the example of the bone fiducial 502 serving as the origin marker.

The bone fiducial 502 is shown as a planar element having a pattern disposed thereon, though other shapes for the bone fiducial 502 may be used (e.g., a square block with a pattern on each face of the block). The bone fiducial 502 may be attached to the bone 500 in any suitable form (e.g., a fastener, such as a screw). The pattern of the bone fiducial is designed to provide information regarding the orientation of the bone fiducial 502 in the three-dimensional coordinate space of the view of the arthroscope 408. More particularly, the pattern is selected such that the orientation of the bone fiducial 502, and thus the orientation of the underlying bone 500, may be determined from images captured by the arthroscope 408 and attached camera head 410 (FIG. 4).

The probe fiducial 506 (an instrument fiducial) is shown as a planar element attached to the touch probe 504. The touch probe 504 may be used, as discussed more below, to "paint" the surface of the bone 500 as part of the registration of the bone 500 to the three-dimensional bone model, and the touch probe 504 may also be used to indicate revised-tunnel entry locations in the case of intraoperative changes to the tunnel paths. The probe fiducial 506 is shown as a planar element having a pattern disposed thereon, though other shapes for the probe fiducial 506 may be used (e.g., a square block surrounding the touch probe 504 with a pattern on each face of the block). The pattern of the probe fiducial 506 is designed to provide information regarding the orientation of the probe fiducial 506 in the three-dimensional coordinate space of the view of the arthroscope 408. More particularly, the pattern is selected such that the orientation of the probe fiducial 506, and thus the location of the tip of the touch probe 504, may be determined from images captured by the arthroscope 408 and attached camera head 410 (FIG. 4).

Other instruments within the view of the arthroscope 408 may also have respective instrument fiducials, such as the drill wire 424 (FIG. 4) and aimer 426 (FIG. 4), but the additional instruments are not shown so as not unduly complicate the figure. Moreover, in addition to or in place of tracking location based on the view through the arthroscope 408, the location of the distal end of one or more of the instruments may be tracked by other methods and systems. For example, for devices that rigidly extend out of the surgical site (e.g., the aimer 426 (FIG. 4)), the location may be tracked by an optical array coupled to the aimer and viewed through the camera 412 (FIG. 4), such as a stereoscopic camera. The location within the three-dimensional coordinate space of the camera 412 is then transformed into the three-dimensional coordinate space of the view of the example arthroscope to determine location of the distal end within the surgical site.

The images captured by the arthroscope 408 and attached camera head 410 are subject to optical distortion in many forms. For example, the visual field between distal end of the arthroscope 408 and the bone 500 within the surgical site is filled with fluid, such as bodily fluids and saline used to distend the joint. Many arthroscopes have one or more lenses at the distal end that widen the field of view, and creating wider field of view causes a "fish eye" effect in the captured images. Further, the optical elements within the arthroscope (e.g., rod lenses) may have optical aberrations inherent to the manufacturing and/or assembly process. Further still, the camera head 410 may have various optical elements for focusing the images receives onto the capture array, and the various optical elements may have aberrations inherent to the manufacturing and/or assembly process. As explained in further detail in Quist, in example systems and methods, prior to use within each surgical procedure, the endoscopic optical system is calibrated to account for the various optical distortions. In an example calibration procedure, the example surgical controller 418 creates a characterization function that characterizes optical distortion between the calibration target and the capture array within the camera head 410. The characterization function may include a calibration for determining orientation of fiducial markers visible within the surgical site (e.g., bone fiducial 502, probe fiducial 506) by way of the arthroscope 408 and attached camera head 410.

The next example step in the intraoperative procedure is the registration of the bone model(s). That is, during the planning stage, imaging (e.g., MRI) of the knee takes place, including the relevant anatomy like the lower portion of the femur, the upper portion of the tibia, and the articular cartilage. The imaging can be segmented such that a volumetric model or three-dimensional model of the anatomy is created from cross-sectional images captured during the imaging. More specifically to the example of ACL repair, and specifically selecting a tunnel path through the femur, a three-dimensional bone model of the lower portion of the femur is created during the planning.

During the intraoperative repair, the three-dimensional bone models and the cross-sectional images are provided to the surgical controller 418. Again using the example of ACL repair, and specifically computer-assisted navigation for tunnel paths through the femur, the three-dimensional bone model of the lower portion of the femur is provided to the surgical controller 418. Thus, the surgical controller 418 receives the three-dimensional bone model, and assuming the arthroscope 408 is inserted into the knee by way of a port through the patient's skin, the surgical controller 418 also receives video images of the femur. In accordance with example methods, the surgical controller 418 may be provided, and thus may receive, the cross-sectional images captured during the planning.

In order to relate the three-dimensional bone model to the images received by way of the arthroscope 408 and camera head 410, the surgical controller 418 registers the three-dimensional bone model to the images of the femur received by way of the arthroscope 408 and camera head 410. The surgical controller 418 may also register the cross-sectional images to the image of the femur received by way of the arthroscope 408 and camera head 410.

In accordance with example methods, where the origin marker is to be a bone fiducial, a fiducial marker or bone fiducial (e.g., bone fiducial 502 of FIG. 5) is attached to the femur. The bone fiducial placement is such that the bone fiducial is within the field of view of the arthroscope 408, but in a location spaced apart from the expected tunnel entry/exit point through the lateral condyle. More particularly, in example cases the bone fiducial is placed within the intercondylar notch superior to or above the expected location of the tunnel through lateral condyle.

Figure 6:
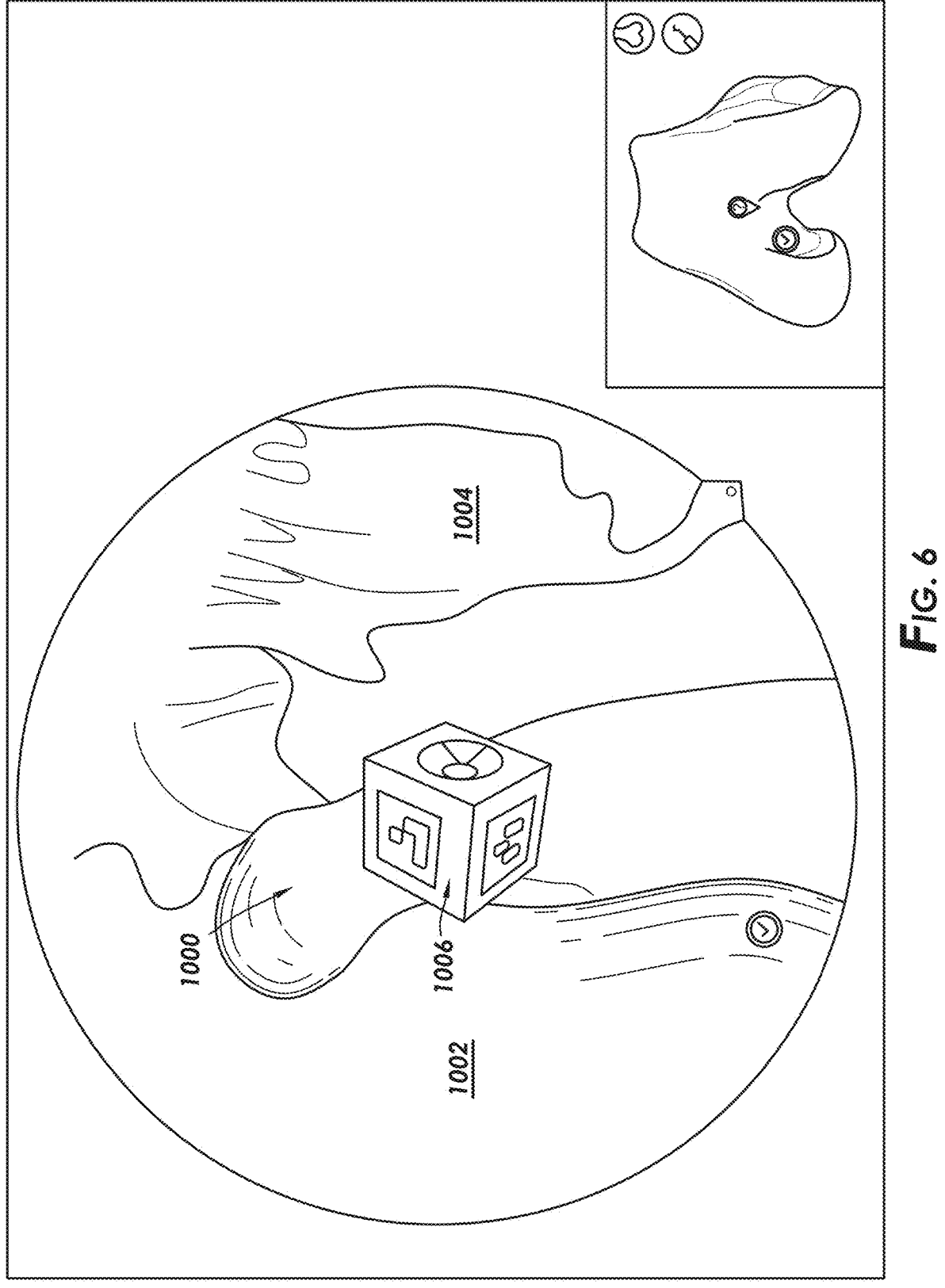
FIG. 6 is an example video display showing portions of a femur and having visible therein a bone fiducial, in accordance with at least some embodiments.

FIG. 6 is an example video display showing portions of a femur and a bone fiducial 1006. The display may be shown, for example, on the display device 414 (FIG. 4) associated with the device cart 402 (FIG. 4), or any other suitable location. In particular, visible in FIG. 6 is a femoral notch or intercondylar notch 1000, a portion of the lateral condyle 1002, a portion the medial condyle 1004, and an example bone fiducial 1006. The bone fiducial 1006 is a fiducial comprising a cube member. Of the six outer faces of the cube member, the bottom face is associated with an attachment feature (e.g., a screw). The bottom face will be close to or will abut the bone when the bone fiducial 1006 is secured in place, and thus will not be visible in the view of the arthroscope 408 (FIG. 4). The outer face opposite the bottom face includes a placement feature used to hold the bone fiducial 1006 prior to placement, and to attach the bone fiducial 1006 to the underlying bone. Of the remaining four outer faces of the cube member (only two of the remaining faces are visible), each of the four outer faces has a machine-readable pattern thereon, and in some cases each machine-readable pattern is unique. Once placed, the bone fiducial 1006 represents a fixed location on the outer surface of the bone in the view of the arthroscope 408, even as the position of the arthroscope 408 is moved and changed relative to the bone fiducial 1006. Initially, the location of the bone fiducial 1006 with respect to the three-dimensional bone model is not known to the surgical controller 418, hence the need for the registration of the three-dimensional bone model.

In or order to relate or register the bone visible in the video images to the three-dimensional bone model, the surgical controller 418 (FIG. 4) is provided and thus receives a plurality of locations of an outer surface of the bone. For example, the surgeon may touch a plurality of locations using the touch probe 504 (FIG. 5). As previously discussed, the touch probe 504 comprises a probe fiducial 506 (FIG. 5) visible in the video images captured by the arthroscope 408 (FIG. 4) and camera head 410 (FIG. 4). The physical relationship between the distal end of the touch probe 504 and the probe fiducial 506 is known by the surgical controller 418, and thus as the surgeon touches each of the plurality of locations on the outer surface of the bone, the surgical controller 418 gains an additional "known" locations of the outer surface of the bone relative to the bone fiducial 1006 (or, in other examples, whatever origin marker is being used). Given that the touch probe 504 is a relatively inflexible instrument, in other examples the tracking of the touch probe 504 may be by optical tracking of an optically-reflective array outside the surgical site (e.g., tracking by the camera 412 (FIG. 4)) yet attached to the portion of the touch probe 504 inside the surgical site.

In some cases, particularly when portions of the outer surface of the bone are exposed to view, receiving the plurality of locations of the outer surface of the bone may involve the surgeon "painting" the outer surface of the bone. "Painting" is a term of art that does not involve application of color or pigment, but instead implies motion of the touch probe 504 when the distal end of the touch probe 504 is touching bone.

Further details of registering a three-dimensional bone model to images of a bone received by way of the arthroscope 408 and camera head 410 will not be described further herein. However, a number of systems, methods and procedures for conducting such registration with respect to a bone fiducial are described in Quist.

Using the three-dimensional bone model an operative plan may be created that comprises a planned-tunnel path through the bone, including locations of the apertures into the bone that define the ends of the tunnel. In some cases, however, the surgeon may elect not to use planned-tunnel path, and thus elect not use the planned entry location, exit location, or both. Such an election can be based any of a number of reasons. For example, intraoperatively the surgeon may not be able to access the entry location for the planned-tunnel path, and thus may need to move the entry location to ensure sufficient access. As another example, during the intraoperative procedure the surgeon may determine that the planned tunnel entry location is misaligned with the attachment location of the native ACL to the femur. Further still, during the intraoperative procedure the surgeon may determine the tunnel entry location is too close to the posterior wall of the femur, increasing the likelihood of a bone chip sometimes referred to as a "back wall blowout." Regardless of the reason for the election to change the tunnel path, in example systems the surgical controller 418 may enable the surgeon to intraoperatively select a revised-tunnel entry, a revised-tunnel exit (if needed), and thus a revised-tunnel path through the bone.

A number of systems, methods and procedures for intra-operatively selecting a revised-tunnel entry, a revised-tunnel exit, and thus a revised-tunnel path through the bone are described in Quist.

During intraoperative selection of a revised-tunnel entry, a revised-tunnel exit, and thus a revised-tunnel path through the bone, it may be useful for a surgeon to be provided, on a display device such as display device 414, with one or more of the cross-sectional images of the bone. More particularly, during such intraoperative selection, it may be useful for the one or more cross-sectional images of the bone to be automatically selected for display depending on the position and orientation of an instrument with respect to the bone. In this way, the surgeon is automatically provided with cross-sectional views into the bone that correspond with the position and orientation of the instrument with respect to the bone.

Alternatively, or in addition to the display of the one or more cross-sectional images of the bone, it may be useful to display the three-dimensional bone model positioned and oriented on the display device depending on the position and orientation of an instrument with respect to the bone.

Alternatively, or in addition to the display of the one or more cross-sectional images of the bone and/or display of the three-dimensional bone model positioned and oriented on the display device depending on the position and orientation of the instrument with respect to the bone, it may be useful to display one or more indicia in association with the selected cross-sectional images of the bone and/or the three-dimensional bone model, the one or more indicia positioned and/or oriented with respect to the cross-sectional images of the bone and/or the three-dimensional bone model depending on the position and/or orientation of the instrument with respect to the bone. The indicia may provide a visual representation of the position and orientation of the instrument with respect to the bone. The indicia may provide a visual representation of just the position of a tip of the instrument with respect to the bone.

A number of systems, methods and procedures for computer guidance for and creation of the actual tunnel are described in Quist. Computer guidance for creation of the actual tunnel may include guidance for drilling of an initial or pilot tunnel using a drill wire (e.g., drill wire 424 (FIG. 4)), and then using the drill wire as guide wire for one or more reamers to increase the diameter of the pilot tunnel to form the full-diameter actual tunnel though the bone. In some cases the actual tunnel has a counterbore associated with the intercondylar notch to accommodate the width of the autograft, and in such cases an additional reamer may be used to create the counterbore.

During creation of the actual tunnel through the bone, it may be useful for a surgeon to be provided, on a display device such as display device 414, one or more of the cross-sectional images of the bone. More particularly, during creation of the actual tunnel through the bone, it may be useful for the one or more cross-sectional images of the bone to be automatically selected for display depending on the position and orientation of an instrument such as a drill wire (e.g., drill wire 424 (FIG. 4)) with respect to the bone. In this way, the surgeon is automatically provided with cross-sectional views into the bone that correspond with the position and orientation of the instrument with respect to the bone.

Alternatively, or in addition to the display of the one or more cross-sectional images of the bone, it may be useful to display the three-dimensional bone model automatically positioned and oriented on the display device depending on the position and orientation of an instrument, such as the drill wire, with respect to the bone.

Alternatively, or in addition to the display of the one or more cross-sectional images of the bone and/or display of the three-dimensional bone model positioned and oriented on the display device depending on the position and orientation of the instrument with respect to the bone, it may be useful to display one or more indicia in association with the selected cross-sectional images of the bone and/or the three-dimensional bone model, the one or more indicia positioned and/or oriented with respect to the cross-sectional images of the bone and/or the three-dimensional bone model depending on the position and/or orientation of the instrument with respect to the bone.

Figure 7A:
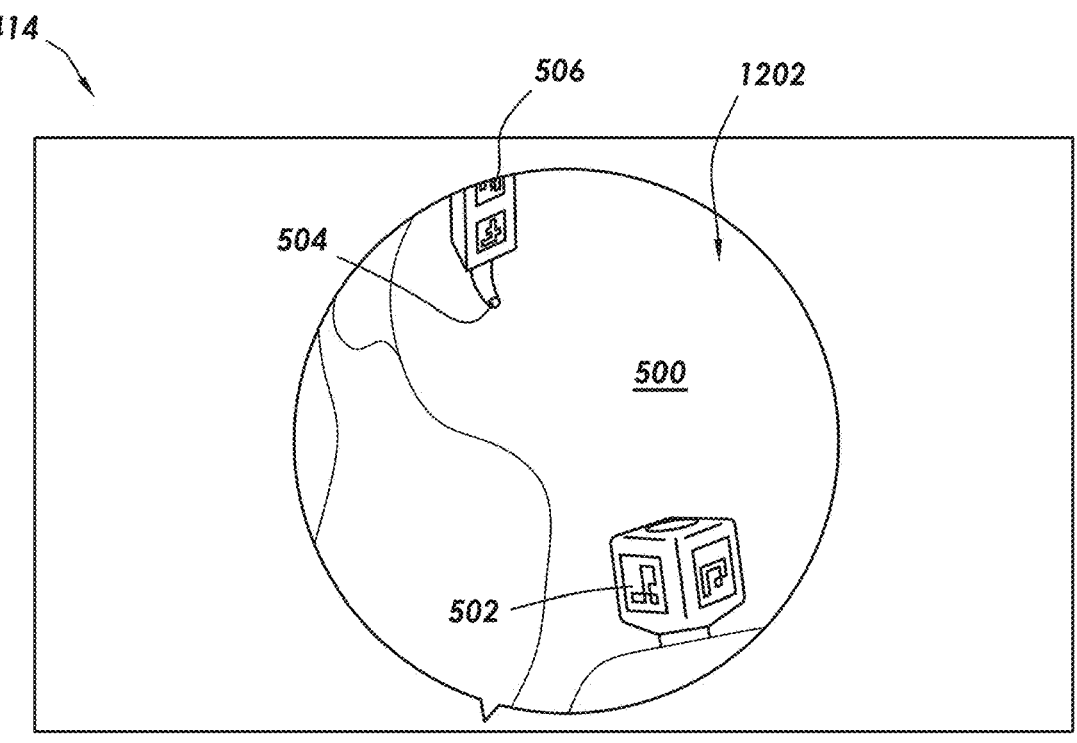
FIG. 7A is an example video display showing portions of a femur and having visible therein a bone fiducial, in accordance with at least some embodiments.

FIG. 7A is an example video display device 414 showing an image of a bone 500 received by way of the arthroscope 408 and camera head 410. This figure captures the image as a single frame of a video stream of frames received from the arthroscope 408 and camera head 410 and displayed in real-time during a surgical procedure. Also shown in the image along with bone 500 in the surgical site are a probe fiducial 506 (i.e. an instrument fiducial) of a touch probe 504 having a respective pattern, and a bone fiducial 502 (i.e. the origin marker) having a respective pattern attached to bone 500. As described herein, the pattern of the probe fiducial 506 is designed to provide information regarding the orientation of the probe fiducial 506 in the three-dimensional coordinate space of the view of the arthroscope 408. More particularly, the pattern enables the orientation of the probe fiducial 506, and the location of the tip of the touch probe 504, to be determined from the images.

Figure 7B:
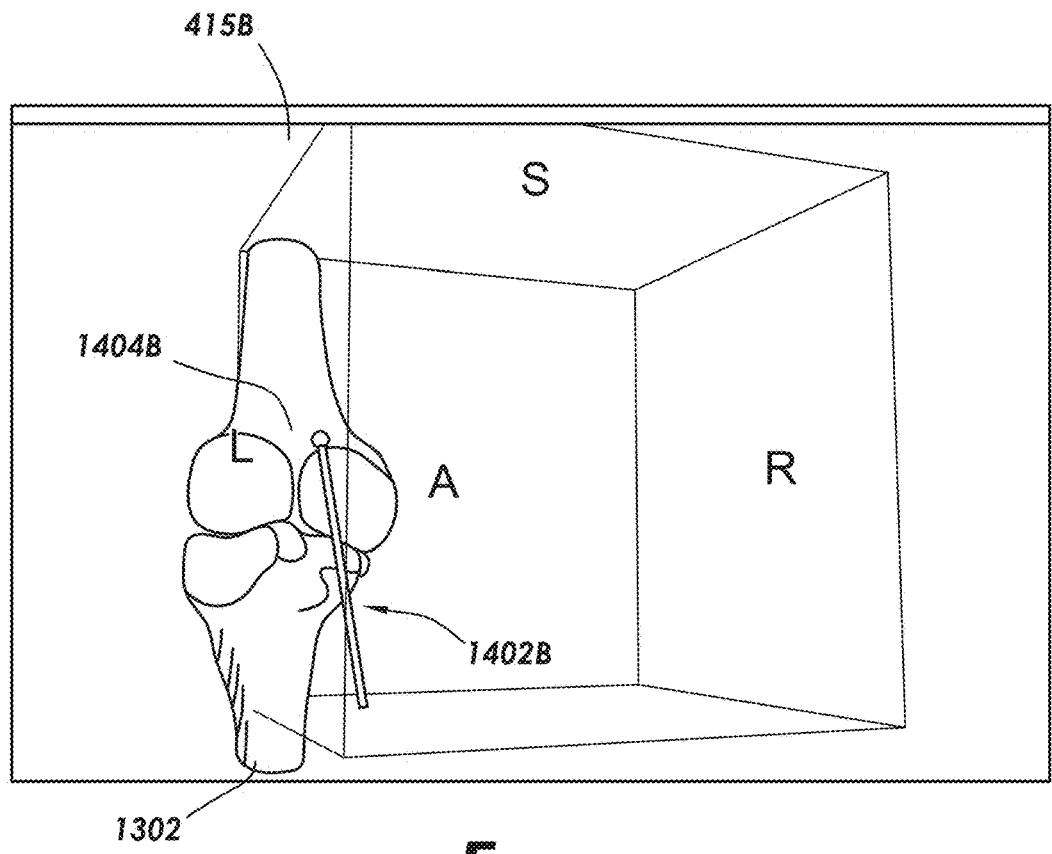
FIG. 7B is an example video display of a three-dimensional bone model corresponding to the femur shown in the video display of FIG. 7A.

FIG. 7B is an example video display 415B showing an image of a three-dimensional bone model 1302 corresponding to bone 500 in FIG. 7A. This figure captures the image as a single frame of a video stream of frames displayed in real-time during a surgical procedure. In this image, the three-dimensional bone model 1302 is positioned and oriented on the video display 415B depending on the position and orientation of the touch probe 504 with respect to the bone 500, as shown in FIG. 7A. Furthermore, an indicia 1402B—in this example a graphical straight line terminating at a termination point 1404B located on the exterior of the three-dimensional bone model 1302—is displayed in association with the three-dimensional bone model 1302 depending on the position and orientation of the touch probe 504 with respect to the bone 500. The termination point 1404B of the indicia 1402B with respect to the three-dimensional bone model 1302 corresponds to the location of the tip of the touch probe 504 with respect to the bone 500. Furthermore, the indicia 1402B has an orientation—the trajectory of the graphical straight line, in particular—with respect to the three-dimensional bone model 1302 that corresponds to the orientation of the probe fiducial 506 with respect to the bone 500. As the surgeon intraoperatively modifies the location and/or orientation of the touch probe 504 with respect to the bone fiducial 502, the video display 415B is caused to display a modified location and/or orientation of the indicia 1402B with respect to the three-dimensional bone model 1302.

In some examples, the location and/or orientation of the three-dimensional bone model 1302 in the video display may be modified responsive to the surgeon intraoperatively modifying the location and/or orientation of the touch probe 504 with respect to the bone fiducial 502. In one example, corresponding to a modification of location and/or orientation of the probe fiducial 506 with respect to the bone fiducial 502, the location and orientation of the indicia 1402B may remain fixed in the video display while the location and/or orientation of the three-dimensional bone model 1302 is modified. In another example, the location and/or orientation of both the indicia 1402B and the three-dimensional bone model 1302 may be modified corresponding to a modification of location and/or orientation of the probe fiducial 506 with respect to the bone fiducial 502.

In some examples, a user such as a surgeon may be provided with an adjustable setting enabling the user to choose to maintain the three-dimensional bone model 1302 in a particular fixed position and/or orientation in the video display 415B such that only the position and/or orientation of the indicia 1402B is modified corresponding to the modification of location and/or orientation of the probe fiducial 506 with respect to the bone fiducial 502, while the three-dimensional bone model 1302 keeps a fixed position and orientation. In some examples, the user may be provided with an adjustable setting enabling the user to choose to maintain the indicia 1402B in a particular fixed position and/or orientation in the video display 415B such that only the position and/or orientation of the three-dimensional bone model 1302 is modified corresponding to the modification of location and/or orientation of the probe fiducial 506 with respect to the bone fiducial 502. The user may wish to toggle between adjustable settings according to preference and/or intraoperative task. For example, during drilling a surgeon may wish to maintain the three-dimensional bone model 1302 in a fixed position in the video display 415B while permitting the position and/or orientation of the indicia 1402B to be modified corresponding to modifications in the position and/or orientation of the probe fiducial 506 with respect to the bone fiducial 502. As another example, during probing a surgeon may wish to permit the three-dimensional bone model 1302 to be modified in position and/or orientation corresponding to modifications in the position and/or orientation of the touch probe 504 such that the portion of the face of the three-dimensional model 1302 brought squarely into video in the video display 415B corresponds to the portion of the bone 500 that the touch probe 504 is extending normal to. In this way, the surgeon can, using the instrument—whether a touch probe 504, a drill wire, or some other instrument having a fiducial or a feature/configuration that is otherwise uniquely discernable—position and orient both the three-dimensional bone model 1302 and the indicia 1402B in the video display 415B in manners that facilitate the intraoperative needs of the surgeon, and can also modify these positions and orientations depending on different needs during a procedure.

In some examples, an indicia overlaid atop of the three-dimensional bone model and/or an indicia overlaid atop one or more of the cross-sectional images being displayed may be directly manipulated by the surgeon, such that a counterpart indicia having a corresponding position and/or orientation is overlaid atop an endoscopic view of the bone, such as the view shown in FIG. 7A. In this way, the surgeon can use the cross-sectional images and/or the three-dimensional bone model to locate a point, which can thereafter be highlighted in the endoscopic view.

Figure 8:
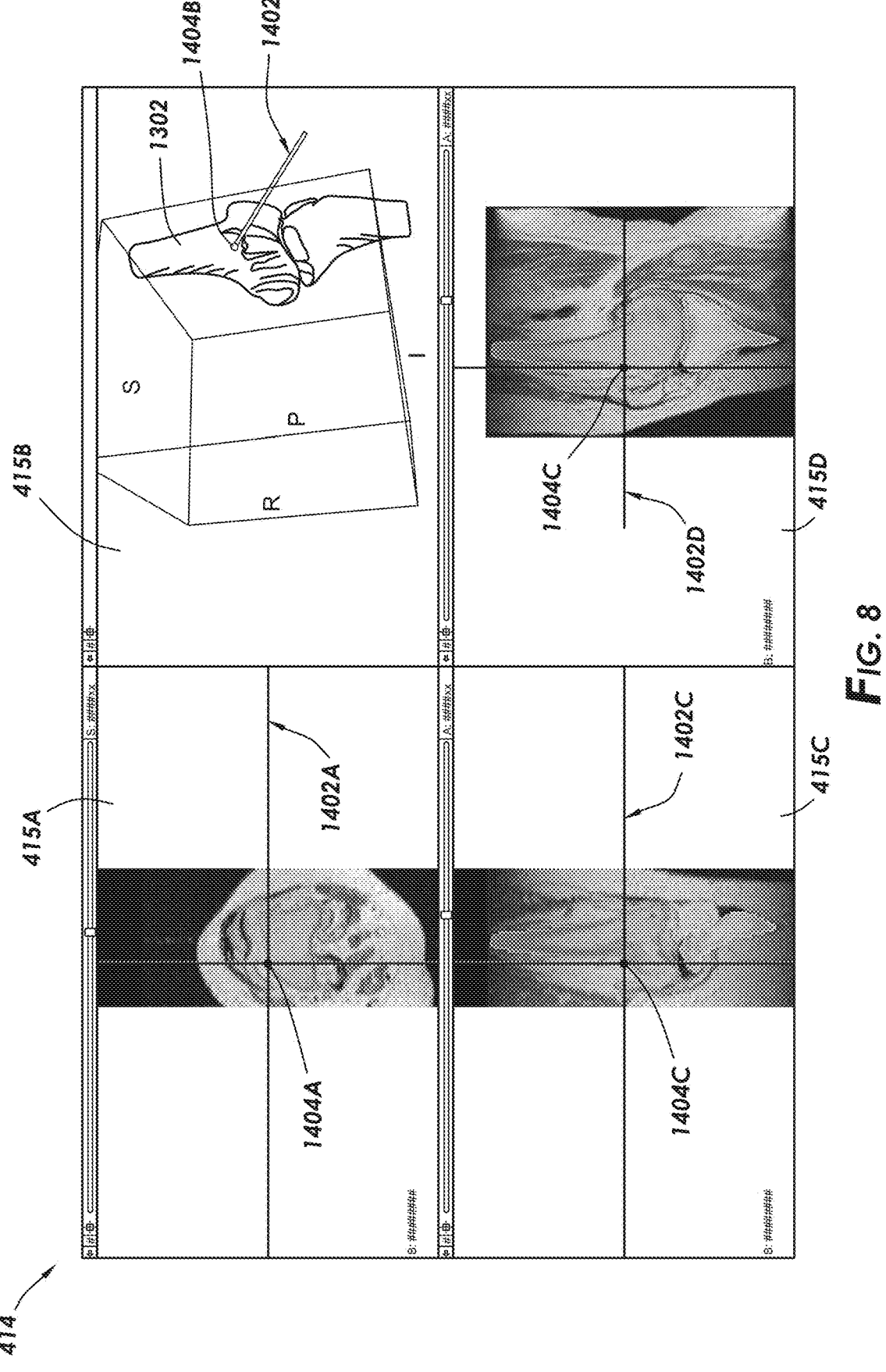
FIG. 8 shows three cross-sectional images and a three-dimensional bone model shown in respective quadrants of the video display and corresponding to the femur shown in the video display of FIG. 7A.

FIG. 8 is an example video display device 414 showing display of three cross-sectional images 415A, 415C, 415D of the bone 500, and display of a three-dimensional model 415B, each in respective quadrants of the video display device 414. Each of the three cross-sectional images 415A, 415C, 415D of bone 500 has been captured using a computed tomography process along a respective one of the axial, sagittal and coronal axes. It will be appreciated that other methods of capturing cross-sectional images of bone 500 along these axes are available, such as MRI images captured using a magnetic resonance imaging process. Each of the three cross-sectional images 415A, 415C, 415D is overlaid with respective indicia 1402A, 1402C, 1402D—in this embodiment, each being cross-hairs having respective intersection points 1404A, 1404C, 1404D. The intersection points 1404A, 1404C, 1404D correspond to the (X,Y)

position in each respectively displayed slice S of the tip of the instrument depending on the position of the instrument fiducial—such as probe fiducial 506—with respect to bone fiducial 502. Whereas indicia 1402B in display 415B displays both the location of the tip of the instrument and its orientation, as each of cross-sectional images 415A, 415C, and 415D displays two-dimensional image information, only the location of the tip of the instrument, and not its orientation, is represented.

As described herein, each of the three cross-sectional images 415A, 415C, 415D is a member of a respective set of cross-sectional images each captured at different points along the same one of the axial, sagittal, or coronal axes during a preoperative image capture process. The cross-sectional images may be electronically stored in association with each other as a set according to a particular file format, such as a DICOM (Digital Imaging and Communication in Medicine) standard file format. For medical imaging, images as captured may be stored without compression or using particular standardized lossless compression schemes thereby to avoid the introduction of artifacts that may be attributable to the compression and decompression processes themselves. The entire set of cross-sectional images, containing an axial series of cross-sectional images, a sagittal series of cross-sectional images, and a coronal series of cross-sectional images, may be labelled with information about the patient, as well as other information corresponding to image capture conditions, such as image slice thickness, image dimensions with respect to the actual anatomy that was imaged, and others.

Figure 12:
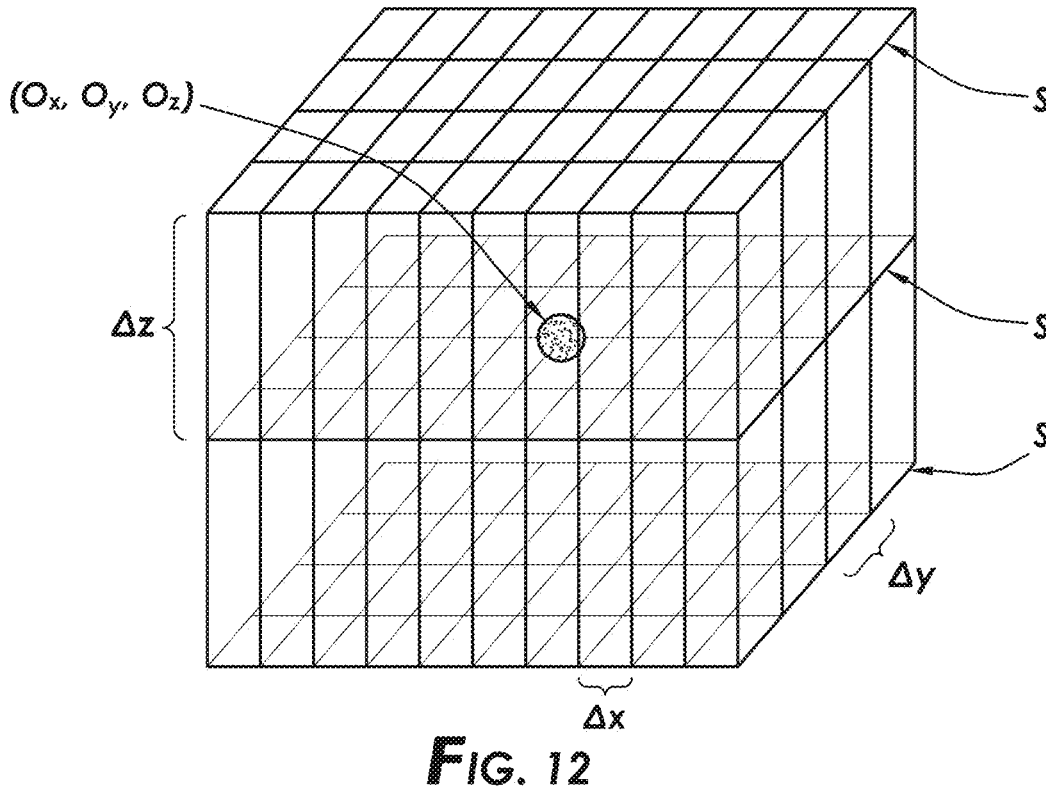
FIG. 12 is a conceptual drawing of a series of cross-sectional medical images and parameters corresponding to the series.

FIG. 12 is a conceptual drawing of a series of cross-sectional medical images and parameters corresponding to the series. Three representations of images, or slices S each having pixels at respective (X,Y) positions, are shown stacked along the axial plane axis. The parameter $\Delta z$ represents the slice thickness (or more particularly the distance between slices), the parameter $\Delta x$ represents the pixel spacing in the horizontal direction, and the parameter $\Delta y$ represents the pixel spacing in the vertical direction. The point $(O_x, O_y, O_z)$ represents the (X,Y,S) position corresponding to the origin RAS, or world coordinate, space. That is, a (0,0,0) location with respect to (or in) the anatomy to be imaged corresponds to the point $(O_x, O_y, O_z)$ in the cross-sectional images.

The image slice thickness corresponds to the distance between adjacent cross-sectional images in a given series captured along a respective axis. For example, if the entire set of cross-sectional images in the axial series spanned a 5-inch length, and there were a total of 10 images in the axial series, then the slice thickness for the axial series would be 5/10=0.5 inches. While this simple example is provided here it is the case that, in practice, the number of cross-sectional images along a given axis will be generally far greater with a correspondingly far lower slice thickness, thereby to permit greater granularity of imaging within the bone.

The particular file format may enable each of the cross-sectional images to have a file name and/or header enabling labeling according to whether they are axial series, sagittal series or coronal series images, and according to their slice order along their respective axis. In this way, cross-sectional images along a particular axis may be displayed in order on the video display, one after another, responsive to user selection. A user may thereby be provided with the opportunity to navigate to and from a particular slice through the bone, as though sequencing through frames of a video. Images may otherwise be navigated-to non-sequentially, as the user wishes.

Each cross-sectional image is generally comprised of a two-dimensional plane of pixels. As a convention used in this description, for each of the cross-sectional images along the axial axis, the Y position of each pixel is defined by the position of the entire image as a slice along the axial axis, and each pixel in the slice has an unique (X, Z) location and respective pixel value. Similarly, for each of the cross-sectional images along the sagittal axis, the X position of each pixel is defined by the position of the entire image as a slice along the sagittal axis, and each pixel in the slice has an unique (Y, Z) location and respective pixel value. Additionally, for each of the cross-sectional images along the coronal axis, the Z position of each pixel is defined by the position of the entire image as a slice along the coronal axis, and each pixel in the slice has an unique (X, Y) location and respective pixel value.

Figure 11:
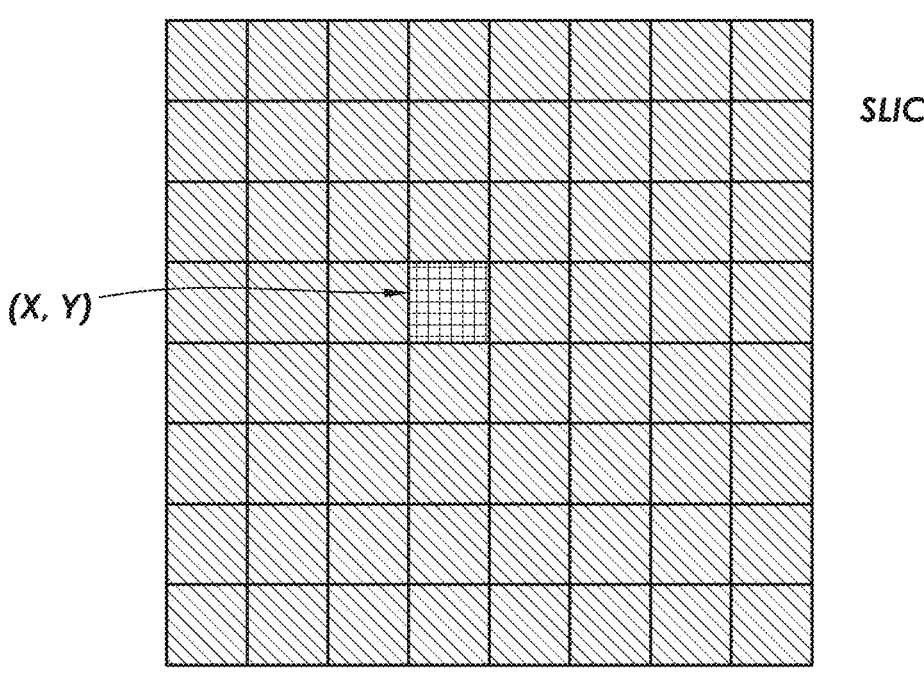
FIG. 11 is a conceptual drawing of a single cross-sectional medical image, or "slice" S, having several pixels and single one of which is highlighted at the location (X, Y)

Moreover, as a convention used in this description, along each axis, a given pixel location may be characterized as (X,Y,S), where S is a particular image slice and (X,Y) is a two-dimensional location along that particular image slice, as shown in FIG. 11. Therefore, for example, a pixel at a location (10,20,30) along the axial axis is not the same as a pixel at a location (10,20,30) along the sagittal axis, and neither of these pixels are the same as a pixel at a location (10,20,30) along the coronal axis.

A PACS (Picture Archiving and Communication System) may be used to select, display and navigate through the cross-sectional images, to display multiple axes' images at once on a single display, to magnify images, and to conduct other image selection and display functions. A PACS may be made available intraoperatively for use by a surgeon during a procedure, so that the cross-sectional images may be manually selected and displayed. In accordance with this example, a cross-sectional image along each of the axial, sagittal, and coronal axes is automatically selected and displayed depending on the location of the instrument tip with respect to the bone, as determined based on the location of the instrument fiducial with respect to the bone fiducial. As the instrument tip is moved with respect to the bone, different ones of the cross-sectional images along respective axes may be selected and displayed. In this example, the PACS may be separate from the surgical controller 418 but may be provided by the surgical controller 418 with control signals that contain one or more localization codes corresponding to cross-sectional images to be displayed by the PACS based on a mapping. In other examples, the PACS system may be integrated with the surgical controller 418 such that the cross-sectional images are selected and displayed by the surgical controller 418 on the display device 414 based on a mapping.

Figure 13:
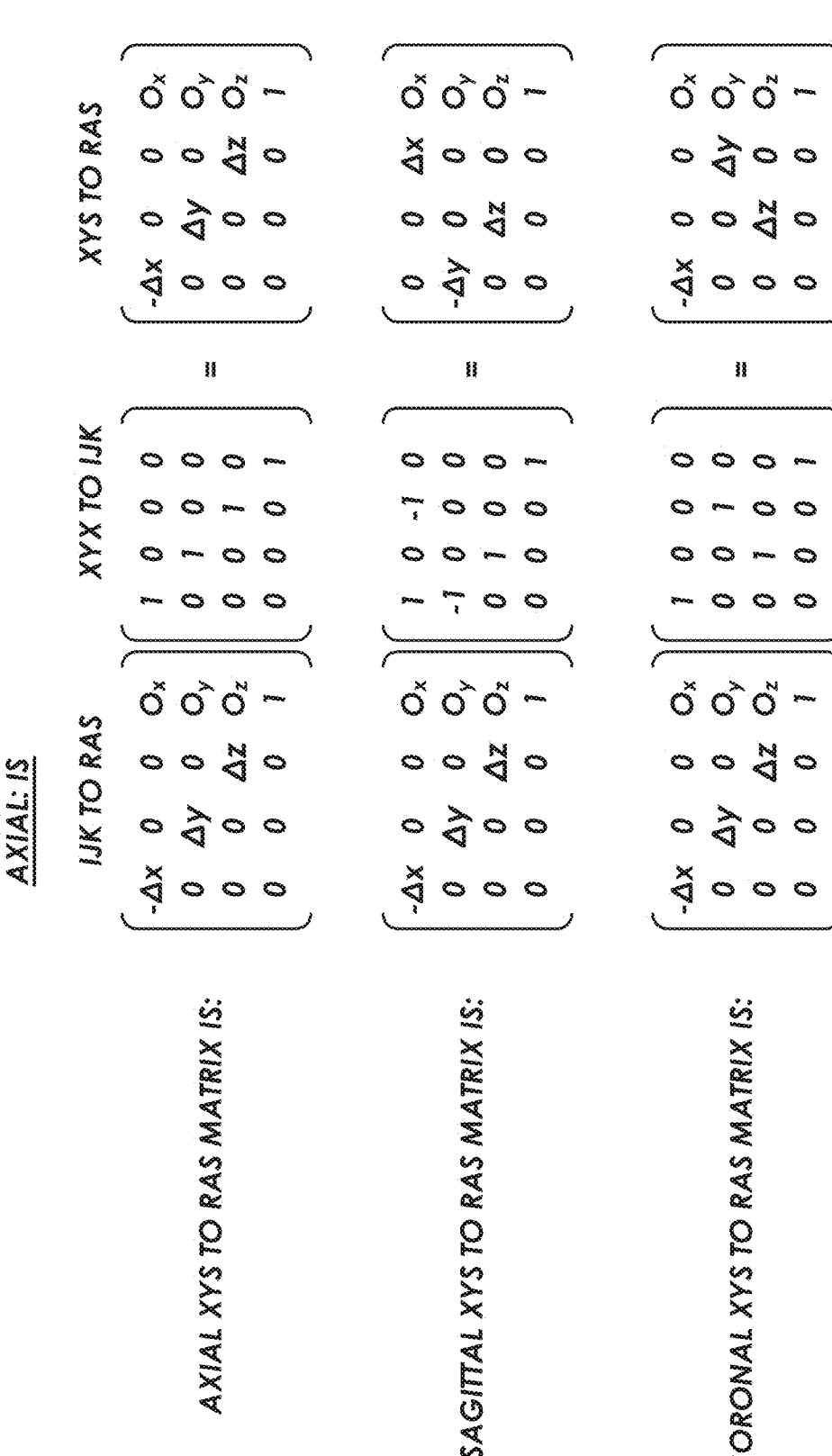
FIG. 13 is a set of matrices that codify a mapping for the axial axis between a RAS/world coordinate system representing the coordinate system of the surgical site, and an (X,Y,S) coordinate system representing the (X,Y) position and a slice S in a series of cross-sectional images.

In this example, a mapping may be created between a world coordinate system/RAS (x,y,z) corresponding to the surgical site, and the (X,Y,S) pixel plane of the cross-sectional images. FIG. 13 is a set of matrices that codify a mapping for the axial axis between a RAS/world coordinate system representing the coordinate system of the surgical site, and an (X,Y,S) coordinate system representing the (X, Y) position and a slice S in a series of cross-sectional images.

With this mapping, as the position of an instrument tip in the RAS coordinate system is moved, a particular cross-sectional image (or "slice" S) in one, two or each of the three cross-sectional image dimensions (i.e., axial, sagittal, and coronal axes) may be automatically selected and displayed in lieu of previously-displayed content. For example, as a surgeon moves an instrument tip deeper along the z axis of the world coordinate system, such as may be done when advancing an instrument such as a drill wire further into a bone, successive cross-sectional images along the coronal axis may be selected and displayed in lieu of previously-displayed cross-sectional images along the coronal axis. Furthermore, the mapping may enable display of an indicia at, or in respect of, a particular (X,Y) position in the selected and displayed slice S corresponding to the position of the instrument tip in the world coordinate system, in lieu of a previous (X,Y) position in the same slice. For example, as a surgeon moves an instrument tip in an x direction in the world coordinate system while maintaining the instrument tip at the same z axis depth, as might be done while moving an instrument such as a touch probe along a surface to consider different tunnel entry points, the same coronal axis slice S may be held constant, but the indicia's (X, Y) position on that coronal axis slice S may change thereby to indicate the instrument tip position in that same coronal axis cross-sectional image. In this example, as a surgeon moves the instrument tip in the x and/or y directions in the world coordinate system while maintaining the instrument tip at the same z axis depth, different axial axis and/or sagittal axis slices S may be selected and displayed while the coronal axis slice S is held constant and the indicia's (X, Y) position in that coronal axis slice S changes. Furthermore, an indicia's (X, Y) position in each of the axial and/or sagittal axis slices S being displayed depends on the instrument tip position in the world coordinate system.

As briefly explained above, in order to relate the three-dimensional bone model to the images received by way of the arthroscope 408 and camera head 410, the surgical controller 418 registers the three-dimensional bone model to the images of the femur received by way of the arthroscope 408 and camera head 410. In this example, the surgical controller 418 also registers the cross-sectional images to the image of the femur. In particular, a mapping is created that relates the cross-sectional images and the images of the femur received by way of the arthroscope 408 and camera head 410.

Such a mapping may be direct as in FIG. 13, such that the mapping enables locations in images of the femur to be transformed directly to (X,Y) locations in respective slices S in the axial, sagittal, and coronal series' of cross-sectional images. Such a mapping may alternatively be via a mapping to the three-dimensional bone model, such that locations of a tip of the instrument in respective video frames determined based on the position and orientation of the instrument fiducial in the video frames may be first transformed to counterpart locations with respect to the three-dimensional bone model and then, in turn, transformed from the locations with the respect to the three-dimensional bone model to a respective one, two or three cross-sectional images. The cross-sectional images to which the locations with respect to the three-dimensional bone model may be one, two or all of the axial series, the sagittal series, and the coronal series in the set of cross-sectional images of the bone that was used to create the three-dimensional bone model itself. One, two or all three of the axes' cross-sectional images may be displayed, during a procedure, simultaneous with the display of the images of the femur received by way of the arthroscope 408 and camera head 410. These may all be displayed in regions of the same display, or displayed in regions of different displays.

Figure 9:
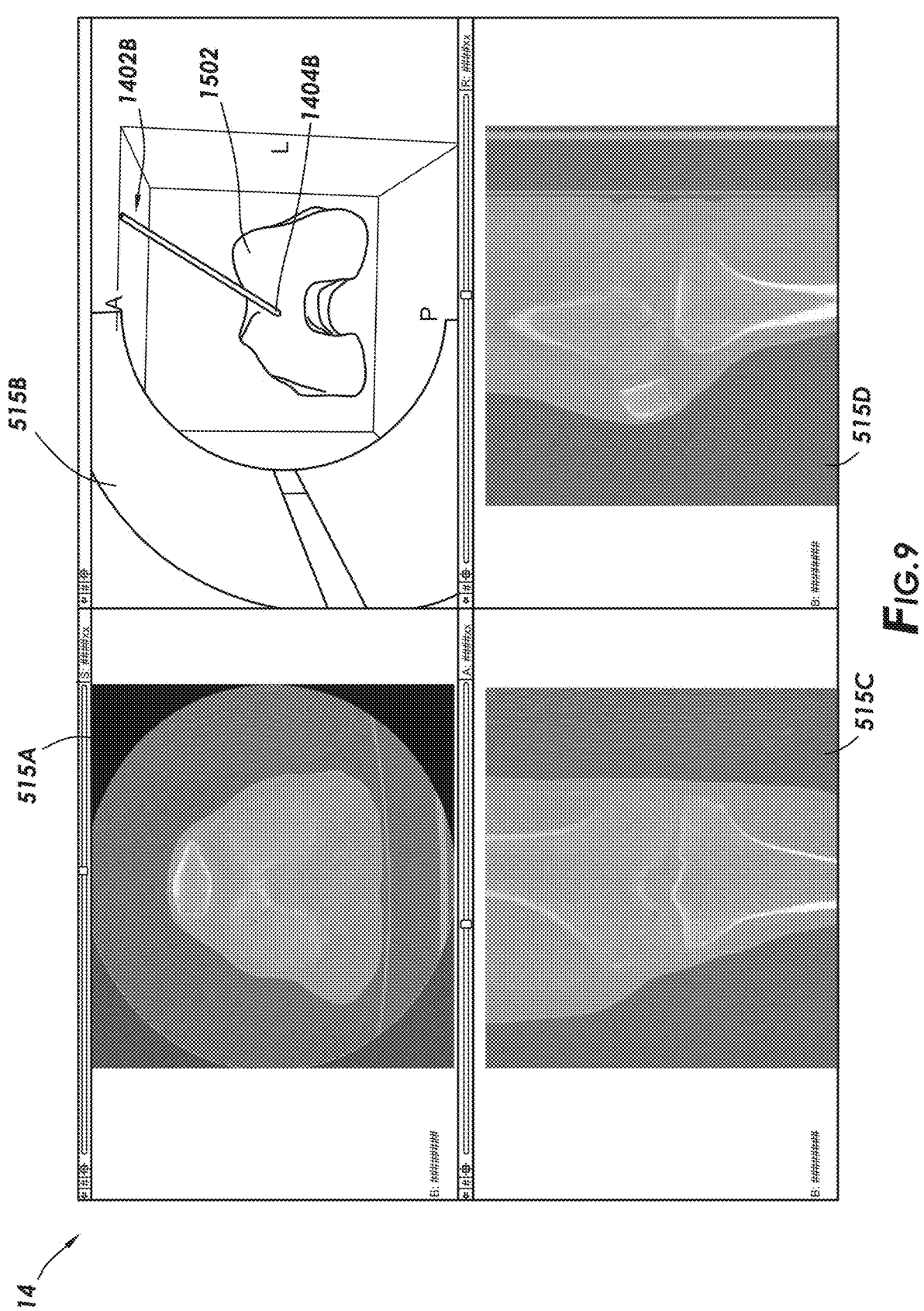
FIG. 9 shows three cross-sectional images and a three-dimensional bone model shown in respective quadrants of the video display and corresponding to the femur shown in the video display of FIG. 7A.

Turning to FIG. 9, there is shown another example video display device 514 showing display of three cross-sectional images 515A, 515C, 515D of a bone, and display of images 515B of a three-dimensional bone model 1502, each in respective quadrants of the video display device 514. Video display device 514 may be the same device as, or a different device from, video display device 414. Each of the three cross-sectional images 515A, 515C, 515D of the bone has been captured using a computed tomography process along a respective one of the axial, sagittal and coronal axes. Unlike in FIG. 8, no indicia overlies any of the three cross-sectional images 515A, 515C, 515D. However, an indicia 1402B overlies the three-dimensional bone model 1502. Indicia 1402B in display 515B displays both the tip of the instrument and its orientation.

Because of the registration of the three-dimensional bone model to the bone, and the relationship between the cross-sectional images and the three-dimensional bone model, measurements of the bone can be made intraoperatively. For example, a surgeon may contact the bone in the surgical site at a first location on the bone with the tip of an instrument, such as the touch probe. This first location may be registered by the surgeon, and mapped to a first location on the three-dimensional bone model. This first location on the three-dimensional bone model may, in turn, be mapped to a first (X,Y,S) location in each series of the set of cross-sectional images. A second location on the bone may be contacted by the surgeon and similarly registered, such that the mapping can provide a second (X,Y,S) location in each series of the set of cross-sectional images. As the set of cross-sectional images is associated with information corresponding to the image capture conditions, including image dimensions with respect to the actual anatomy that was imaged, a distance between the first and second (X,Y,S) locations in the cross-sectional images can be measured. Multiple (X,Y,S) locations may be registered by the surgeon to trace more complex paths, which can each be measured for distance. Where two-dimensional/three-dimensional areas/volumes are formed from such points/traces by the surgeon, these areas/volumes may also be measured. Such first, second and additional locations, as well as the areas/volumes traced may be displayed in association with the three-dimensional bone model and/or the cross-sectional images, as well as graphical traces between them, to represent the trace made by the surgeon when registering the multiple points touched by the instrument tip. Measurements of length, curvature, area and volume, may be recorded as well as displayed to the surgeon during the procedure.

Figure 10:
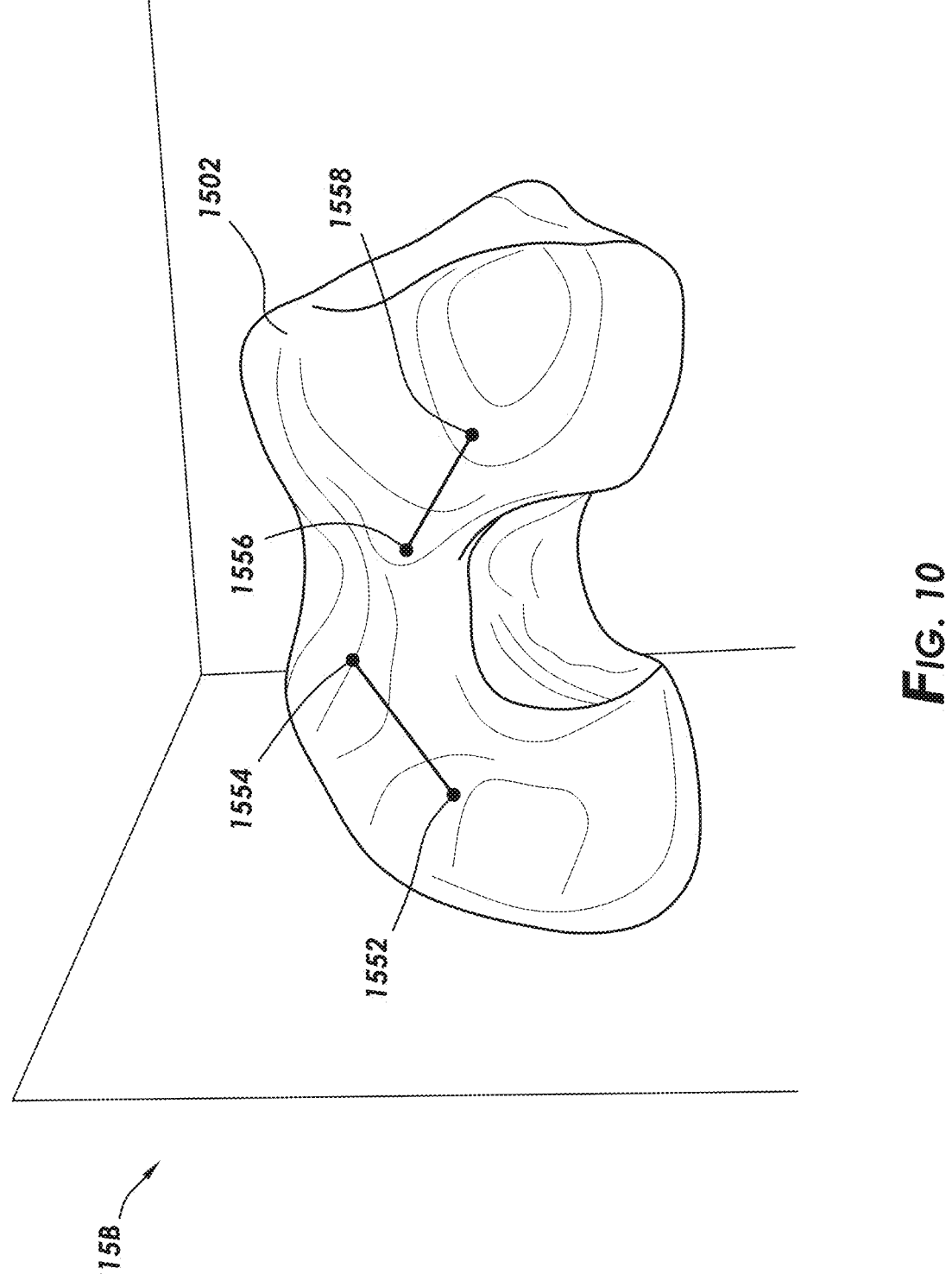
FIG. 10 shows the three-dimensional bone model of FIG. 9 in isolation and further shows measurable markup curves, or "traces", extending between respective endpoints on the three-dimensional bone model.

For example, FIG. 10 shows example video display 515B displaying the three-dimensional bone model 1502. FIG. 10 further shows measurable markup curves, or "traces", extending between respective endpoints on the three-dimensional bone model. In particular, a first trace is delimited by endpoints 1552 and 1554, and a second trace is delimited by endpoints 1556 and 1558. The length of the first trace may be measured by calculating a distance between endpoints 1552 and 1554 in and through the corresponding cross-sectional images, and the length of the second trace may be measured by calculating a distance between endpoints 1556 and 1558 in and through the corresponding cross-sectional images.

In examples described herein a bone fiducial, such as bone fiducial 502 coupled to the bone, is deployed as an origin marker that specifies the origin and orientation of the three-dimensional coordinate space of the view the arthroscope. However, other forms of origin marker are possible. For example, unique anatomical structure within the field of view of the arthroscope may be used as an origin marker. In order for unique anatomical structure to serve reliably, like a bone fiducial, as an origin marker, the unique anatomical structure should be reliably discernable from other anatomical structure that may come within the field of view of the arthroscope, should persist over at least the time of the surgical procedure, and should be three-dimensional. In this way, processing of images captured via an arthroscope of the surgical site and the unique anatomical structure can reliably determine the position and orientation of the unique anatomical structure, and thus the origin of the three-dimensional coordinate space, from various arthroscopic perspectives over the duration of the surgical procedure.

Because unique bone structure within the surgical site that is not to be modified by the surgical procedure itself can indeed be reliably discernable from other bone structure, can generally persist over time, and is three-dimensional, such unique bone structure may serve as an origin marker. In order to deem a particular volume of unique bone structure or other form of anatomical structure, as an origin marker, a surgeon may capture arthroscopic video frames of the volume of unique bone structure or other form of anatomical structure from different perspectives during an origin marker registration phase, and the surgical controller may process the arthroscopic video frames to identify features such as lines, peaks, valleys and the like in multiple of the video frames and generate a three-dimensional model of the unique bone structure or other unique anatomical structure that can be used as the origin marker. With a three-dimensional model for the origin marker having been determined, during the subsequent phases of the surgical procedure the surgical controller is able to process image frames to locate, scale, and orient the unique bone structure or other unique anatomical structure with respect to the three-dimensional model for the origin structure, thereby to track the location and orientation of the three-dimensional coordinate system.

While unique bone structures are one example of a unique anatomical structure suitable for use as an origin marker, other tissue structures that may be a combination of bone structures and another kind or kinds of tissue, or that may be entirely non-bone tissue structures, may serve as origin markers. It will also be appreciated that other non-anatomical markers that are not drilled into bone as is a bone fiducial, may be used as origin markers. For example, a temporary marking or set of markings with a three-dimensional character may be imparted to the anatomical structure within the surgical site and that may persist through the surgical procedure without having to have been drilled into the bone itself as is a bone fiducial. Variations are possible.

Software and Hardware

Figure 14:
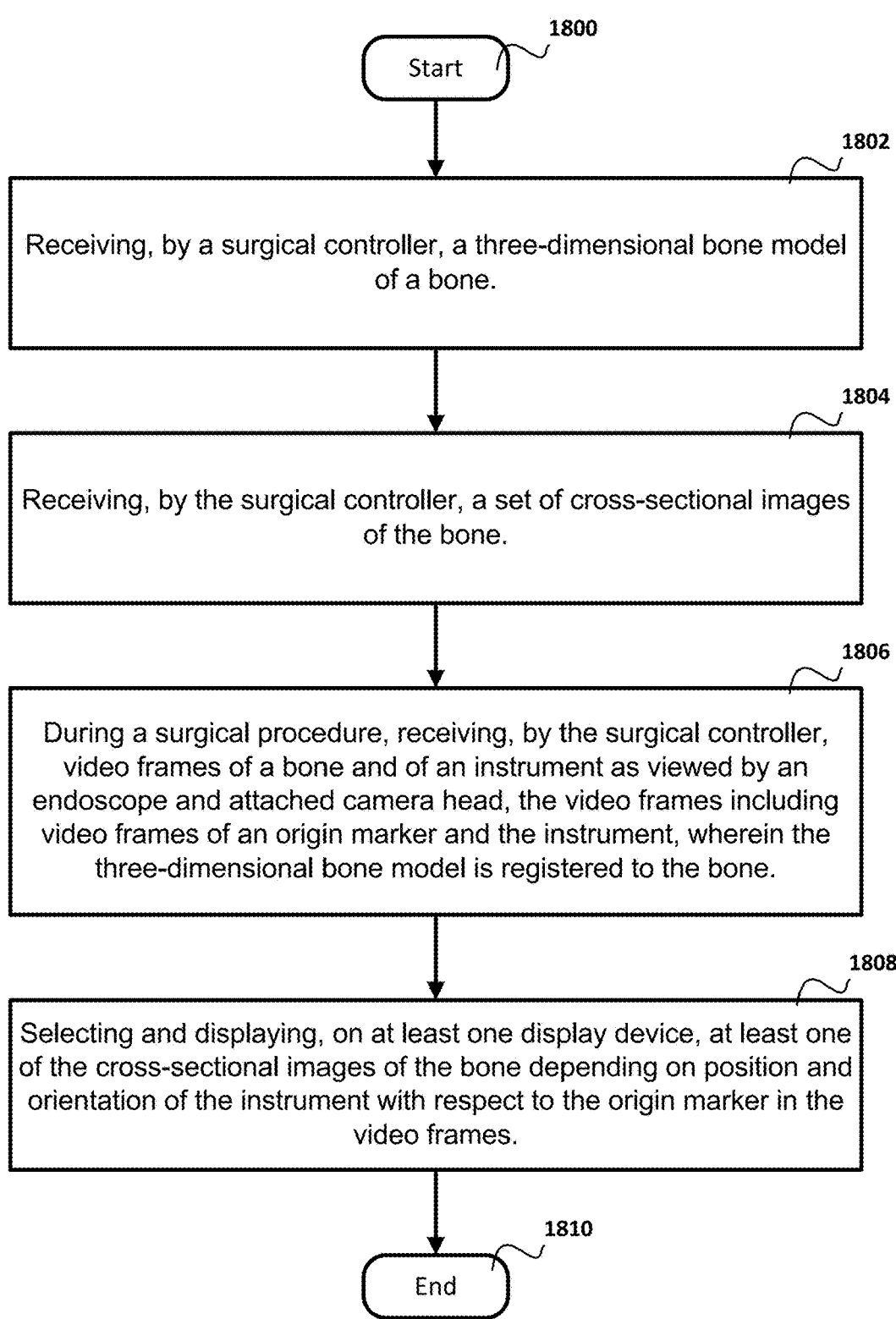
FIG. 14 shows an intraoperative method in accordance with at least some embodiments.

FIG. 14 shows an intraoperative method, in accordance with at least some embodiments. In particular, the method starts (block 1800) and comprises: receiving, by a surgical controller, a three-dimensional bone model of a bone (block 1802); receiving, by the surgical controller, a set of cross-sectional images of the bone (block 1804); and during a surgical procedure: receiving, by the surgical controller, video frames of a bone and of an instrument as viewed by an endoscope and attached camera head, the video frames including video frames of an origin marker and the instrument, wherein the three-dimensional bone model is registered to the bone (block 1806); and selecting and displaying, on at least one display device, at least one of the cross-sectional images of the bone depending on position and orientation of the instrument with respect to the origin marker in the video frames (block 1808). Thereafter, the method ends (block 1810). The example method may be implemented by computer instructions executed with the processor of computer system, such as the surgical controller 418 (FIG. 4).

Figure 15:
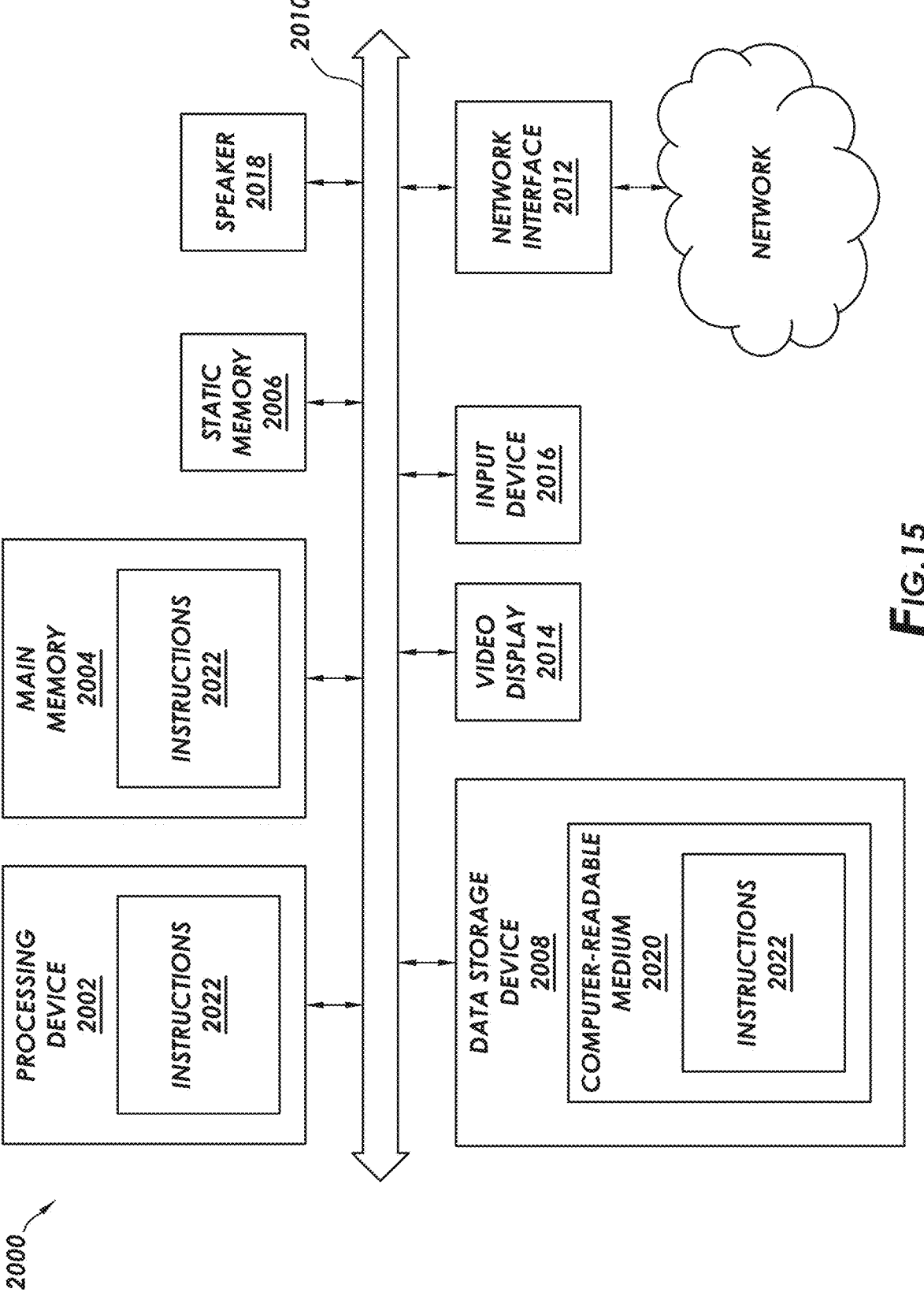
FIG. 15 shows a computer system in accordance with at least some embodiments.

FIG. 15 shows an example computer system 2000. In one example, computer system 2000 may correspond to the surgical controller 418, a tablet device within the surgical room, or any other system that implements any or all the various methods discussed in this specification. The computer system 2000 may be connected (e.g., networked) to other computer systems in a local-area network (LAN), an intranet, and/or an extranet (e.g., device cart 402 network), or at certain times the Internet (e.g., when not in use in a surgical procedure). The computer system 2000 may be a server, a personal computer (PC), a tablet computer or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 2000 includes a processing device 2002, a main memory 2004 (e.g., read-only memory (ROM), flash memory, dynamic random access memory (DRAM) such as synchronous DRAM (SDRAM)), a static memory 2006 (e.g., flash memory, static random access memory (SRAM)), and a data storage device 2008, which communicate with each other via a bus 2010.

Processing device 2002 represents one or more general-purpose processing devices such as a microprocessor, central processing unit, or the like. More particularly, the processing device 2002 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 2002 may also be one or more special-purpose processing devices such as an application specific integrated circuit (ASIC), a field programmable gate array (FPGA), a digital signal processor (DSP), network processor, or the like. The processing device 2002 is configured to execute instructions for performing any of the operations and steps discussed herein. Once programmed with specific instructions, the processing device 2002, and thus the entire computer system 2000, becomes a special-purpose device, such as the surgical controller 418.

The computer system 2000 may further include a network interface device 2012 for communicating with any suitable network (e.g., the device cart 402 network). The computer system 2000 also may include a video display 2014 (e.g., display device 414), one or more input devices 2016 (e.g., a microphone, a keyboard, and/or a mouse), and one or more speakers 2018. In one illustrative example, the video display 2014 and the input device(s) 2016 may be combined into a single component or device (e.g., an LCD touch screen).

The data storage device 2008 may include a computer-readable storage medium 2020 on which the instructions 2022 (e.g., implementing any methods and any functions performed by any device and/or component depicted described herein) embodying any one or more of the methodologies or functions described herein is stored. The instructions 2022 may also reside, completely or at least partially, within the main memory 2004 and/or within the processing device 2002 during execution thereof by the computer system 2000. As such, the main memory 2004 and the processing device 2002 also constitute computer-readable media. In certain cases, the instructions 2022 may further be transmitted or received over a network via the network interface device 2012.

While the computer-readable storage medium 2020 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An intraoperative method comprising:
receiving, by a surgical controller, a three-dimensional bone model of a bone;
receiving, by the surgical controller, a set of cross-sectional images of the bone; and
during a surgical procedure:
receiving, by the surgical controller, video frames of a bone and of an instrument as viewed by an endoscope and attached camera head, the video frames including video frames of an origin marker and the instrument, wherein the three-dimensional bone model is registered to the bone; and
automatically selecting and displaying, on at least one display device, at least one of the cross-sectional images of the bone depending on position and orientation of the instrument with respect to the origin marker in the video frames.

2. The intraoperative method of claim 1, wherein the origin marker is a bone fiducial coupled to the bone.

3. The intraoperative method of claim 1, wherein origin marker is a unique anatomical structure.

4. The intraoperative method of claim 3, wherein the unique anatomical structure is a unique bone structure.

5. The intraoperative method of claim 1, wherein the video frames include video frames of an instrument fiducial coupled to the instrument, and further wherein the automatically selecting and displaying is depending on position and orientation of the instrument fiducial with respect to the origin marker in the video frames.

6. The intraoperative method of claim 1,
wherein the set of cross-sectional images of the bone include an axial series of cross-sectional images, a sagittal series of cross-sectional images, and a coronal series of cross-sectional images.

7. The intraoperative method of claim 6, wherein the automatically selecting and displaying comprises:
automatically selecting from and displaying the cross-sectional images of the bone from each of the axial series, the sagittal series, and the coronal series.

8. The intraoperative method of claim 1, further comprising:
overlaying, on automatically selected and displayed cross-sectional images, an indicia corresponding to a location of a tip of the instrument at a time of display.

9. The intraoperative method of claim 8, further comprising:

displaying, on the at least one display device, a visual representation of the three-dimensional bone model and a visual representation of a position and an orientation of the instrument with respect to the three-dimensional bone model depending on a position and an orientation of the instrument with respect to the origin marker in the video frames.

10. The intraoperative method of claim 1, wherein the automatically selecting and displaying comprises:

determining locations of a tip of the instrument in respective video frames;

transforming each of the locations of the tip of the instrument in respective video frames to counterpart locations with respect to the three-dimensional bone model;

transforming each of the counterpart locations with respect to the three-dimensional bone model to a respective at least one cross-sectional image in the set of cross-sectional images of the bone; and displaying the respective at least one cross-sectional image.

11. The intraoperative method of claim 10, wherein the set of cross-sectional images of the bone includes an axial series of cross-sectional images, a sagittal series of cross-sectional images, and a coronal series of cross-sectional images; and wherein transforming each of the counterpart locations with respect to the three-dimensional bone model to a respective at least one cross-sectional image in the set of cross-sectional images of the bone comprises, for each of a plurality of the video frames:

transforming each of the counterpart locations with respect to the three-dimensional bone model to each of a corresponding cross-sectional image in the axial series, a corresponding cross-sectional image in the sagittal series, and a corresponding cross-sectional image in the coronal series; and wherein displaying the respective at least one cross-sectional image comprises, for each of the plurality of the video frames:

displaying each of the corresponding cross-sectional image in the axial series, the corresponding cross-sectional image in the sagittal series, and the corresponding cross-sectional image in the coronal series.

12. The intraoperative method of claim 1, wherein the set of cross-sectional images comprises preoperative-captured cross-sectional images.

13. A surgical controller comprising:

processing structure configured to couple to at least one display device;

a memory coupled to the processing structure, the memory storing instructions that, when executed by the processing structure, cause the processing structure to:

receive a three-dimensional bone model of a bone;

receive a set of cross-sectional images of the bone; and during a surgical procedure:

receive video frames of a bone and of an instrument as viewed by an endoscope and attached camera head, the video frames including video frames of an origin marker and the instrument, wherein the three-dimensional bone model is registered to the bone; and automatically select and display, on the at least one display device, at least one of the cross-sectional images of the bone depending on position and orientation of the instrument with respect to the origin marker in the video frames.

14. The surgical controller of claim 13, wherein the origin marker is a bone fiducial coupled to the bone.

15. The surgical controller of claim 13, wherein the origin marker is a unique anatomical structure.

16. The surgical controller of claim 15, wherein the unique anatomical structure is a unique bone structure.

17. The surgical controller of claim 13, wherein the video frames include video frames of an instrument fiducial coupled to the instrument, and further wherein the automatically selecting and displaying is depending on position and orientation of the instrument fiducial with respect to the origin marker in the video frames.

18. The surgical controller of claim 13, wherein the set of cross-sectional images of the bone includes an axial series of cross-sectional images, a sagittal series of cross-sectional images, and a coronal series of cross-sectional images.

19. The surgical controller of claim 18, wherein instructions that, when executed by the processing structure, cause the processing structure to automatically select and display comprises:

instructions that, when executed by the processing structure, cause the processing structure to automatically select from and display the cross-sectional images of the bone from each of the axial series, the sagittal series, and the coronal series.

20. The surgical controller of claim 13, wherein the memory stores instructions that, when executed by the processing structure, cause the processing structure to:

overlay, on automatically selected and displayed cross-sectional images, an indicia corresponding to a location of a tip of the instrument at a time of display.

21. The surgical controller of claim 20, wherein the memory stores instructions that, when executed by the processing structure, cause the processing structure to:

display, on the at least one display device, a visual representation of the three-dimensional bone model and a visual representation of a position and an orientation of the instrument with respect to the three-dimensional bone model depending on the position and orientation of the instrument with respect to the origin marker in the video frames.

22. The surgical controller of claim 13, wherein the instructions that, when executed by the processing structure, cause the processing structure to automatically select and display comprises instructions that, when executed by the processing structure, cause the processing structure to:

determine locations of a tip of the instrument in respective video frames;

transform each of the locations of the tip of the instrument in respective video frames to counterpart locations with respect to the three-dimensional bone model;

transform each of the counterpart locations with respect to the three-dimensional bone model to a respective at least one cross-sectional image in the set of cross-sectional images of the bone; and display the respective at least one cross-sectional image.

23. The surgical controller of claim 22, wherein the set of cross-sectional images of the bone includes an axial series of cross-sectional images, a sagittal series of cross-sectional images, and a coronal series of cross-sectional images; and wherein the instructions that, when executed by the processing structure, cause the processing structure to transform comprises instructions that, when executed by the processing structure, cause the processing structure to:

for each of a plurality of the video frames:

transform each of the counterpart locations with respect to the three-dimensional bone model to each of a corresponding cross-sectional image in the axial series, a corresponding cross-sectional image in the sagittal series, and a corresponding cross-sectional image in the coronal series; and wherein the instructions that, when executed by the processing structure, cause the processing structure to display comprises instructions that, when executed by the processing structure, cause the processing structure to:

display each of the corresponding cross-sectional image in the axial series, the corresponding cross-sectional image in the sagittal series, and the corresponding cross-sectional image in the coronal series.

24. The surgical controller of claim 13, wherein the set of cross-sectional images comprises preoperative-captured cross-sectional images.

* * * * *